United States Patent
Pierce et al.

(10) Patent No.: US 9,717,758 B2
(45) Date of Patent: Aug. 1, 2017

(54) HIGH-AFFINITY DMF5 T CELL RECEPTOR (TCR) VARIANTS

(71) Applicants: University of Massachusetts, Boston, MA (US); University of Notre Dame du Lac, Notre Dame, IN (US)

(72) Inventors: Brian G. Pierce, Wayland, MA (US); Zhiping Weng, Wellesley, MA (US); Brian M. Baker, Granger, IN (US)

(73) Assignees: University of Massachusetts, Boston, MA (US); University of Notre Dame du Lac, Notre Dame, IN (US)

( * ) Notice: Subject to any disclaimer, the term of this patent is extended or adjusted under 35 U.S.C. 154(b) by 540 days.

(21) Appl. No.: 14/280,308

(22) Filed: May 16, 2014

(65) Prior Publication Data

US 2014/0341809 A1 Nov. 20, 2014

Related U.S. Application Data

(60) Provisional application No. 61/824,831, filed on May 17, 2013.

(51) Int. Cl.
*A61K 39/395* (2006.01)
*A61K 35/17* (2015.01)
*C07K 14/705* (2006.01)

(52) U.S. Cl.
CPC ............ *A61K 35/17* (2013.01); *C07K 14/705* (2013.01)

(58) Field of Classification Search
None
See application file for complete search history.

(56) References Cited

U.S. PATENT DOCUMENTS

2012/0071420 A1  3/2012  Robbins et al.

OTHER PUBLICATIONS

Bahar et al., "Global Dynamics of Proteins: Bridging Between Structure and Function", Annu Rev Biophys, vol. 39:23-42 (2010).
Balgley et al., "Comparative Evaluation of Tandem MS Search Algorithms Using a Target-Decoy Search Strategy", Mol Cell Proteomics, vol. 6:1599-1608 (2007).
Beddoe et al., "Antigen ligation triggers a conformational change within the constant domain of the αβ T cell receptor", vol. 30:777-788 (2009).
Borbulevych et al., "TCRs Used in Cancer Gene Therapy Cross-React with MART-1/Melan-A Tumor Antigens via Distinct Mechanisms", J Immunol, vol. 187:2453-2463 (2011).
Boulter et al., "Stable, soluble T-cell receptor molecules for crystallization and therapeutics", Protein Engineering, vol. 16:707-711 (2003).
Chervin et al., "The Impact of TCR-Binding Properties and Antigen Presentation Format on T Cell Responsiveness", J Immunol, vol. 183:1166-1178 (2009).
Chlewicki et al., "High-affinity, Peptide-specific T Cell Receptors can be Generated by Mutations in CDR1, CDR2 or CDR3", Journal of Molecular Biology, vol. 346:223-239 (2005).
Corse et al., "Attenuated T Cell Responses to a High-Potency Ligand In Vivo", PLoS Biology, vol. 8(9):e1000481 (2010).
Corse et al., "Strength of TCR-Peptide/MHC Interactions and In Vivo T Cell Responses", J Immunol, vol. 186:5039-5045 (2011).
Davis et al., "Ligand Recognition by αβ T cell receptors", Annu Rev Immunol, vol. 16:523-544 (1998).
Davis-Harrison et al., "Two different T cell receptors use different thermodynamic strategies to recognize the same peptide/MHC ligand", J Mol Biol, vol. 346:533-550 (2005).
Deng et al., "Structural basis for the recognition of mutant self by a tumor-specific, MHC class II-restricted T cell receptor", Nat Immunol, vol. 8:398-408 (2007).
Ding et al., "Four A6-TCR/Peptide/HLA-A2 Structures that Generate Very Different T Cell Signals Are Nearly Identical", Immunity, vol. 11:45-56 (1999).
Dunn et al., "Directed evolution of human T cell receptor CDR2 residues by phage display dramatically enhances affinity for cognate peptide-MHC without increasing apparent cross-reactivity", Protein Science, vol. 15:710-721 (2006).
Englander et al., "Mechanisms and uses of hydrogen exchange", Curr Opin Struct Biol, vol. 6:18-23 (1996).
Eyal et al., "Anisotropic network model: systematic evaluation and a new web interface", Bioinformatics, vol. 22:2619-2627 (2006).
Frederick et al., "Conformational entropy in molecular recognition by proteins", Nature, vol. 448:325-329 (2007).
Gagnon et al., "T cell receptor recognition via cooperative conformational plasticity", J Mol Biol, vol. 363:228-243 (2006).
Garboczi et al., "Assembly, specific binding, and crystallization of a human TCR-alphabeta with an antigenic Tax peptide from human T lymphotropic virus type 1 and the class I MHC molecule HLA-A2", J Immunol, vol. 157:5403-5410 (1996).
Garcia et al., "The molecular basis of TCR germline bias for MHC is surprisingly simple", Nat Immunol, vol. 10:143-147 (2009).
Garcia et al., "An αβ T Cell Receptor Structure at 2.5 Å and Its Orientation in the TCR-MHC Complex", Science, vol. 274:209-219 (1996).
Haider et al., "Structure-Based Design of a T Cell Receptor Leads to Nearly 100-Fold Improvement in Binding Affinity for pepMHC", Proteins, vol. 74:948-960 (2009).
Hawse et al., "Cutting Edge: Evidence for a Dynamically Driven T Cell Signaling Mechanism", J Immunol, vol. 188:5819-5823 (2012).
Holler et al., "Cd8 T Cell Transfectants That Express a High Affinity T Cell Receptor Exhibit Enhanced Peptide-Dependent Activation", The Journal of Experimental Medicine, vol. 194-1043-1052 (2001).
Holler et al., "In vitro evolution of a T cell receptor with high affinity for peptide/MHC", PNAS, vol. 97:5387-5392 (2000).
Johnson et al., "Gene therapy with human and mouse T-cell receptors mediates cancer regression and targets normal tissues expressing cognate antigen", Blood, vol. 114:535-546 (2009).
Johnson et al., "Gene Transfer of Tumor-Reactive TCR Confers Both High Avidity and Tumor Reactivity to Nonreactive Peripheral Blood Mononuclear Cells and Tumor-Infiltrating Lymphocytes", J Immunol, vol. 177:6548-6559 (2006).
Kawakami et al., "Identification of the Immunodominant Peptides of the MART-1 Human Melanoma Antigen Recognized by the Majority of HLA-A2-restricted Tumor Infiltrating Lymphocytes", J Exp Med, vol. 180:347-352 (1994).

(Continued)

Primary Examiner — Zachary Skelding
(74) Attorney, Agent, or Firm — Fish & Richardson P.C.

(57) ABSTRACT

High-affinity variants of the DMF5 TCR, and methods of use thereof for the treatment and imaging of cancer in a patient.

20 Claims, 2 Drawing Sheets

(56) References Cited

OTHER PUBLICATIONS

Kim et al., "Distinctive CD3 Heterodimeric Ectodomain Topologies Maximize Antigen-Triggered Activation of αβ T Cell Receptors", J Immunol, vol. 185:2951-2959 (2010).

Kim et al., "The αβ T Cell Receptor Is an Anisotropic Mechanosensor", J Biol Chem, vol. 284:31028-31037 (2009).

Kortemme et al., "A simple physical model for binding energy hot spots in protein-protein complexes", PNAS, vol. 99:14116-14121 (2002).

Kuhns et al., "Evidence for a furnctional sidedness to the αβTCR", Proc Natl Acad Sci USA, vol. 107:5094-5099 (2010).

Laine et al., "Allosteric Signaling in the Biotin Repressor Occurs via Local Folding Coupled to Global Dampening of Protein Dynamics", J Mol Biol, vol. 381:89-101 (2008).

Laugel et al., "Design of Soluble Recombinant T Cell Receptors for Antigen Targeting and T Cell Inhibition", The Journal of Biological Chemistry, vol. 280:1882-1892 (2005).

Laugel et al., "Different T Cell Receptor Affinity Thresholds and CD8 Coreceptor Dependence Govern Cytotoxic T Lymphocyte Activation and Tetramer Binding Properties", The Journal of Biological Chemistry, vol. 282:23799-23810 (2007).

Li et al., "Directed evolution of human T-cell receptors with picomolar affinities by phage display", Nature Biotechnology, vol. 23:349-354 (2005).

Ma et al., "Dynamic Allostery: Linkers Are Not Merely Flexible", Structure, vol. 19:907-917 (2011).

Marcsisin et al., "Hydrogen exchange mass spectrometry: what is it and what can it tell us?", Anal Bioanal Chem, vol. 397:967-972 (2010).

Marincola et al., "Analysis of expression of the melanoma-associated antigens MART-1 and gp100 in metastatic melanoma cell lines and in in situ lesions", J Immunother Emphasis Tumor Immunol, vol. 19:192-205 (1996).

Marrack et al., "Evolutionarily conserved amino acids that control TCR-MHC interaction", Annu Rev Immunol, vol. 26:171-203 (2008).

Martinez-Martin et al., "Cooperativity between T cell receptor complexes revealed by conformational mutants of CD3 epsilon", Sci Signal, vol. 11:ra43 (2009).

McMahan et al., "Relating TCR-peptide-MHC affinity to immunogenicity for the design of tumor vaccines", J Clin Invest, vol. 116:2543-2551 (2006).

Morgan et al., "Cancer Regression in Patients After Transfer of Genetically Engineered Lymphocytes", vol. 314:126-129 (2006).

Popovych et al., "Dynamically driven protein allostery", Nat Struct Mol Biol, vol. 13:831-838 (2006).

Robbins et al., "Single and Dual Amino Acid Substitutions in TCR CDRs Can Enhance Antigen-Specific T Cell Functions", J Immunol, vol. 180:6116-6131 (2008).

Robbins et al., "Tumor Regression in Patients With Metastatic Synovial Cell Sarcoma and Melanoma Using Genetically Engineered Lymphocytes Reactive With NY-ESO-1", J Clin Oncol, vol. 29:917-924 (2011).

Rosenberg et al., "Adoptive cell transfer: a clinical path to effective cancer immunotherapy", Nat Rev Cancer, vol. 8:299-308 (2008).

Rudolph et al., "How TCRs bind MHCs, peptides, and coreceptors", Annu Rev Immunol, vol. 24:419-466 (2006).

Schmid et al., "Evidence for a TCR Affinity Threshold Delimiting Maximal CD8 T Cell Function", J Immunol, vol. 184:4936-4946 (2010).

Scott et al., "Disparate degrees of hypervariable loop flexibility control T cell receptor cross-reactivity, specificity, and binding mechanism".

Shilov et al., "The Paragon Algorithm, a Next Generation Search Engine That Uses Sequence Temperature Values and Feature Probabilities to identify Peptides from Tandem Mass Spectra", Mol Cell Proteomics, vol. 6:1638-1655 (2007).

Smock et al., "Sending Signals Dynamically", Science, vol. 324:198-203 (2009).

Stone et al., "T-cell receptor binding affinities and kinetics: impact on T-cell activity and specificity", Immunology, vol. 126:165-176 (2009).

Thomas et al., "Human T cells expressing affinity-matured TCR display accelerated responses but fail to recognize low density of MHC-peptide antigen", Blood, vol. 118:319-329 (2011).

Tobi et al., "Structural changes involved in protein binding correlate with intrinsic motions of proteins in the unbound state", PNAS, vol. 102:18908-18913 (2005).

Tzeng et al., "Dynamic activation of an allosteric regulatory protein", Nature, vol. 462:368-372 (2009).

Van der Merwe, P. A., "Mechanisms for T cell receptor triggering", Nat Rev Immunol, vol. 11:47-55 (2011).

Varani et al., "Solution mapping of T cell receptor docking footprints on peptide-MHC", PNAS, vol. 104:13080-13085 (2007).

Varela-Rohena et al., "Control of HIV-1 immune escape by CD8 T-cells expressing enhanced T-cell receptor", Nat Med., vol. 14:1390-1395 (2008).

Weber et al., "Class II-restricted T cell receptor engineered in vitro for high affinity retains peptide specificity and function", PNAS, vol. 102:19033-19038 (2005).

Zhang et al., "DNA binding alters coactiator interation surfaces of the intact VDR-RXR complex", Nat Struct Mol Biol, vol. 18:556-563 (2011).

Zhang et al., "Genetic engineering with T cell receptors", Adv Drug Deliv Rev, vol. 64:756-762 (2012).

Zhao et al., "High-Affinity TCRs Generated by Phage Display Provide CD4 T Cells with the Ability to Recognize and Kill Tumor Cell Lines", J Immunol, vol. 179:5845-5854 (2007).

HIGH-AFFINITY DMF5 T CELL RECEPTOR (TCR) VARIANTS

CLAIM OF PRIORITY

This application claims the benefit of U.S. Provisional Patent Application No. 61/824,831, filed on May 17, 2013. The entire contents of the foregoing are hereby incorporated by reference herein.

FEDERALLY SPONSORED RESEARCH OR DEVELOPMENT

This invention was made with Government support under Grant Nos. GM067079, GM084884, RR025761, and GM103773 awarded by the National Institutes of Health. The Government has certain rights in the invention.

TECHNICAL FIELD

The present invention relates to high-affinity variants of the DMF5 TCR, and methods of use thereof for the treatment and imaging of cancer in a patient.

BACKGROUND

T cell receptors are heterodimeric immunoglobulin proteins, with approximately 30,000 on the surface of each clonally unique T cell (Janeway, *Immunobiology: the Immune System in Health and Disease.* 6th ed. New York: Garland Science; 2005). The specific binding of αβ TCRs to peptides bound by MHC proteins (pMHC) is a critical step in the antigen-specific T cell-mediated immune response. As with antibodies, the antigen-binding Complementarity Determining Region (CDR) loops are variable, with multiple germ-line segments, junctional combinations, and addition or deletion of nucleotides at these junctions used to generate diversity.

SUMMARY

At least in part, the present invention is based on the development of high-affinity variants of the DMF5 TCR. Thus, provided herein are the high-affinity variants themselves, nucleic acids encoding and host cells expressing the variants, and methods of use thereof.

In one aspect, the invention provides a high-affinity DMF5 T cell receptor variant a chain, wherein the amino acid at position 27 is a Y (αD27Y) or W (αD27W), e.g., a variant comprising SEQ ID NO:1, 3, or 5 with a D27Y or D27W mutation. (Herein, the numbering within the alpha chain is with regard to SEQ ID NO:1; the corresponding amino acid in SEQ ID NO:3 is D49, in SEQ ID NO:5, D27).

In another aspect, the invention provides a high-affinity DMF5 T cell receptor variant β chain, wherein the amino acid at position 95 is a W (βL95W), e.g., a variant comprising SEQ ID NO:2, 4, or 6 with an L95W mutation. Herein, the numbering within the beta chain is with regard to SEQ ID NO:2; the corresponding amino acid in SEQ ID NO:4 is L114; in SEQ ID NO:6, L96).

In yet another aspect, the invention provides a high-affinity DMF5 T cell receptor variant comprising: a high-affinity DMF5 T cell receptor variant α chain, wherein the amino acid at position 27 is a Y (αD27Y) or W (αD27W), and a high-affinity DMF5 T cell receptor variant β chain, wherein the amino acid at position 95 is a W (βL95W).

In another aspect, the invention provides a fusion protein comprising:
a high-affinity DMF5 T cell receptor variant α chain as described herein;
a high-affinity DMF5 T cell receptor variant β chain as described herein; or
a high-affinity DMF5 T cell receptor variant as described herein; linked to
a non-T cell receptor sequence.

In another aspect, the invention provides a therapeutic composition comprising:
a therapeutic agent linked to one or more of:
a high-affinity DMF5 T cell receptor variant α chain as described herein;
a high-affinity DMF5 T cell receptor variant β chain as described herein; or
a high-affinity DMF5 T cell receptor variant as described herein; or
a fusion protein as described herein.

In some embodiments the therapeutic agent is a radioisotope; an anticancer drug such as a genotoxin; or a cytotoxic moiety.

In another aspect, the invention provides compositions comprising:
a detectable moiety linked to one or more of:
a high-affinity DMF5 T cell receptor variant α chain as described herein;
a high-affinity DMF5 T cell receptor variant β chain as described herein; or
a high-affinity DMF5 T cell receptor variant as described herein; or
a fusion protein as described herein.

In some embodiments the detectable moiety is a contrast agent.

In some embodiments the contrast agent is selected from the group consisting of gold, gadolinium, iron oxides, manganese chelates, barium sulfate, iodinated contrast media, microbubbles, and perfluorocarbons.

In another aspect, the invention provides a nucleic acid encoding:
a high-affinity DMF5 T cell receptor variant α chain as described herein;
a high-affinity DMF5 T cell receptor variant β chain as described herein; or
a high-affinity DMF5 T cell receptor variant as described herein; or
a fusion protein as described herein. In some embodiments the nucleic acid also includes one or more of an N-terminal leader sequence, some stuff after our C-terminus to help it reach the membrane, a transmembrane spanning alpha helix, and a C-terminal sequence inside of the cell, e.g., from a wild type human TCR, e.g., as known in the art, e.g., as described in Johnson et al., Blood, 2009, and US 2012/0071420, incorporated herein by reference.

In another aspect, the invention provides a vector, e.g., a retroviral vector, comprising a nucleic acid as described herein.

In another aspect, the invention provides a host cell expressing:
a high-affinity DMF5 T cell receptor variant α chain as described herein;
a high-affinity DMF5 T cell receptor variant β chain as described herein; or
a high-affinity DMF5 T cell receptor variant as described herein; or
a fusion protein as described herein.

In another aspect, the invention provides a host cell comprising a nucleic acid or vector as described herein. In some embodiments the host cell is a peripheral blood lymphocyte (PBL).

In another aspect, the invention provides a method of treating a subject who has melanoma, the method comprising administering to the subject a therapeutically effective amount of a therapeutic composition as described herein.

In another aspect, the invention provides a method of treating a subject who has melanoma, the method comprising administering to the subject a therapeutically effective amount of the host cells as described herein. In some embodiments the host cells are autologous to the subject.

In another aspect, the invention provides a method of treating a subject who has melanoma, the method comprising:

obtaining cells from the subject;

transducing the cells with a vector expressing:

a high-affinity DMF5 T cell receptor variant α chain as described herein;

a high-affinity DMF5 T cell receptor variant β chain as described herein; or a high-affinity DMF5 T cell receptor variant as described herein; or a fusion protein as described herein;

optionally maintaining the cells in culture for a time sufficient for the cells to express the variant or fusion protein and/or to proliferate; and administering a therapeutically effective amount of the cells to the subject thereafter.

In some embodiments the cells are PBLs.

In another aspect, the invention provides a method of detecting the presence of a cancer cell in a subject, the method comprising administering to the subject a detectable amount of a composition comprising a detectable moiety as described herein; and detecting the presence of the composition in the subject; thereby detecting the presence of a cancer cell in the subject.

In some embodiments the detectable moiety can be selected from the group consisting of a radioactive isotope, a magnetic compound, an x-ray absorber, a chemical compound, a biological tag, and a fluorescent molecule. The therapeutic agent can be, e.g., a cytotoxic moiety or an immunomodulatory moiety (e.g., a compound that enhances the immune response to the tumor, e.g., an inflammatory cytokine such as interleukin-1 (IL-1), and tumor necrosis factor-alpha (TNF-a).

In some embodiments, there is a linker between the first portion and the second portion, e.g., a flexible amino acid sequence, e.g., a photolinker.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figures 1A, 1B:
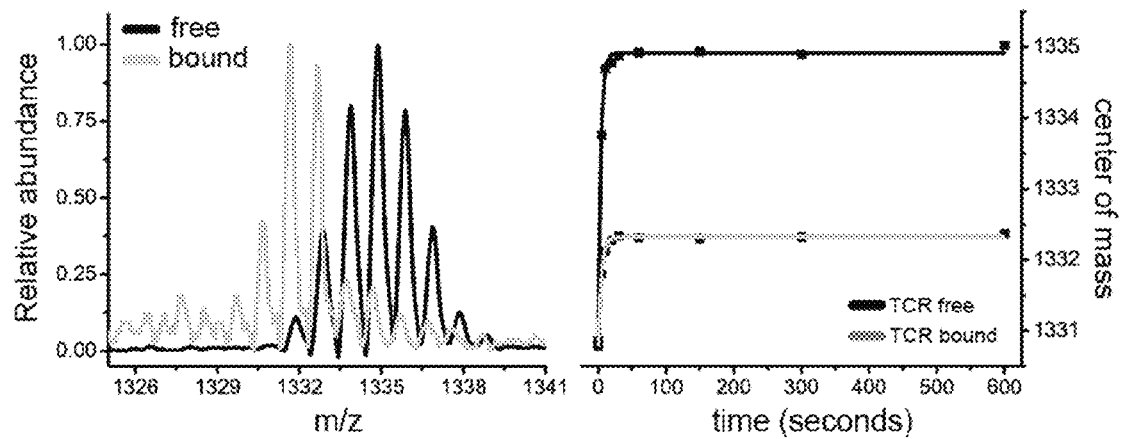
FIGS. 1A-C. Hydrogen/deuterium exchange reveals that the A6 TCR undergoes a global reduction in flexibility upon pMHC binding. (A) MALDI-TOF mass spectra for the fragment of the FG loop (sequence $^{225}$WTQDRAKPVTQ$^{235}$) of A6 free (blue) and bound to Tax/HLA-A2 (red) ten minutes after initiation of hydrogen/deuterium exchange. (B) Time courses for the exchange reaction of the FG loop fragment in panel A demonstrates that in both free and bound A6, exchange follows simple kinetics and is complete within 10 minutes. (C) Percent deuteration of each fragment of free and ligand-bound A6 at the 10 minute time point. Fragments including the CDR and the AB, DE, and FG loops in the constant domains are indicated. The dashed blue and red lines indicate the average deuteration of the free and bound protein, respectively.

The principles of TCR recognition of pMHC have been studied extensively, with the first crystal structures of TCRs in complex with pMHC published in the mid-90's (Garcia et al., Science. 1996; 274(5285):209-19; Garboczi et al., J. Immunol. 1996; 157(12):5403-10). These structures revealed a generally conserved diagonal binding mode that in most cases places the hypervariable CDR3 loops of the TCR over (or near) the center of the peptide (Rudolph et al., Annu Rev Immunol. 2006; 24:419-66). A number of features are shared among the interfaces of TCRs with pMHCs, including particular inter-residue contacts by evolutionarily conserved residues (Marrack et al., Annu Rev Immunol. 2008; 26:171-203), leading to the concept of distinct germline "codons" influencing the TCR/pMHC binding modes (Garcia et al., Nat Immunol. 2009; 10(2):143-7).

Significant effort is underway to develop TCRs as a novel class of biotherapeutics. Therapeutic interest is largely based on using genetic engineering to direct T cells towards antigens of interest, such as those presented either exclusively or preferentially by virally infected or cancerous cells. In some of the most recent work, T cells from patients have been engineered to express a T cell receptor specific for a tumor antigen and infused back into the patient (Rosenberg et al., Nat Rev Cancer. 2008; 8(4):299-308). This exciting approach has shown promise in treating metastatic melanoma (Morgan et al., Science. 2006; 314(5796):126-9; Johnson et al., Blood. 2009; 114(3):535-46) and synovial cell sarcoma (Robbins et al., J Clin Oncol. 2011; 29(7):917-24). Yet there are limitations to this approach, including limited potency due to weak TCR avidity, which can result from the low to moderate affinity TCRs typically maintain towards their cognate antigen: TCR/pMHC affinities are typically in the range of 1-200 µM when measured in solution (Davis et al., Annual review of immunology. 1998; 16:523-44), with the recognition of tumor antigens biased towards the weaker end (Laugel et al., J Biol Chem. 2007; 282(33):23799-810). As T cell sensitivity and potency is generally correlated with TCR affinity (Holler et al., J Exp Med. 2001; 194(8):1043-52; Varela-Rohena et al., Nat Med. 2008; 14(12):1390-5; Zhao et al., J. Immunol. 2007; 179(9):5845-54), this has led to numerous proposals for enhancing immunotherapy by engineering higher affinity receptors. Indeed, in a recent thematic review series on strategies for controlling metastasis and recurrence of cancers, Zhang and Morgan emphasized that "the most critical property for a TCR used for engineering T cells for clinical application is the requirement for high affinity specific recognition" (Zhang and Morgan, Adv Drug Deliv Rev. 2011; 64(8): 756-762).

Recent work has suggested that even small (3-5-fold) improvements in TCR binding affinity can result in stronger in vivo immune responses (Borbulevych et al. (2011) J Immunol 187 p. 2453). In addition to enhancing avidity and sensitivity, high affinity TCRs are independent of the need for coreceptor (Chervin et al., J. Immunol. 2009; 183(2): 1166-78), allowing, for example, the creation of both CD8+ and CD4+ T cells that recognize antigens presented by class I MHC proteins and thus permitting both cytotoxic and helper immune responses against a single antigen (Morgan et al., supra; Robbins et al., supra). High affinity TCRs can also be used to overcome processes associated with cellular escape from immune destruction. For example, Sewell and colleagues described a TCR with high affinity towards an HIV gag epitope that when expressed in T cells is able to direct the killing of cells infected with HIV variants possessing all known HIV gag escape mutants (Varela-Rohena et al., supra).

To overcome their inherent low affinity for peptide/MHC and improve their immunological efficacy, TCRs have been engineered for higher affinity in several studies, primarily via phage display and yeast display (Varela-Rohena et al., supra; Holler et al., Proc Natl Acad Sci USA. 2000; 97(10): 5387-92; Weber et al., Proc Natl Acad Sci USA. 2005; 102(52):19033-8; Li et al., Nat Biotechnol. 2005; 23(3):349-54; Chlewicki et al., J Mol Biol. 2005; 346(1):223-39; Dunn et al., Protein Sci. 2006; 15(4):710-21). These have achieved impressive affinity improvements (approximately 1,000,000-fold in one case), and though antigen specificity appears to be conserved for some high affinity variants (Chlewicki et al., supra; Laugel et al., J Biol Chem. 2005; 280(3):1882-92), there is evidence they can induce off-target T cell responses by raising non-targeted ligand affinities above the activation threshold (Zhao et al., supra; Stone et al., Immunology. 2009; 126(2):165-76). Clinically, such non-specific recognition would lead to dangerous autoimmune reactions, substantially weakening efficacy if not preventing use altogether.

Recent work has shown that very high affinity TCRs, while demonstrating stronger cell killing effects in vitro, can yield low avidity T cells that paradoxically require higher ligand concentrations for activation (Schmid et al., J Immunol. 2010; 184(9):4936-46; Thomas et al., Blood. 2011; 118(2):319-29). This effect has also been measured by vaccinating mice using peptides recognized with a range of TCR affinities; only the peptides recognized by TCRs intermediate affinity induced in vivo tumor protection (McMahan et al., J Clin Invest. 2006; 116(9):2543-51; Corse et al., PLoS Biol. 2010; 8(9)). It is unclear from these studies whether the attenuation of high affinity in vivo T cell response is due to loss of specificity from enhanced recognition of MHC, or other factors related to immune memory, cell differentiation, or signaling mechanisms (Corse et al., Journal of immunology. 2011; 186(9):5039-45). These results as well as others (Zhao et al., supra) suggest that TCR design efforts should emphasize the creation of variants with moderate gains in affinity that fully retain antigen specificity. Indeed, the difference in affinity between the human DMF5 and DMF4 TCRs toward the MART-1 27:35 tumor antigen is only 4-fold, yet in cellular assays DMF5 is substantially more potent (Johnson et al., Journal of Immunology. 2006; 177(9):6548-59), and in clinical trials with genetically-engineered TCRs, DMF5 resulted in higher rates of cancer regression than DMF4 (Johnson et al., Blood. 2009; 114(3): 535-46). Described herein are high-affinity DMF5 variants with improved TCR affinity and specificity.

High-affinity DMF5 Variants

The DMF5 TCR, a high-avidity CD8-independent TCR, was originally isolated from a MART-1:27-35 (MART-1) melanoma Ag-reactive tumor-infiltrating lymphocyte (TIL) clone obtained from the tumors of a melanoma patient (Johnson et al., J. Immunol. 177: 6548-6559, 206). DMF5 is directed against the immunodominant HLA-A2-restricted peptide epitopes corresponding to amino acids 26-35 and 27-35 of the melanoma Ag MART-1 (Kawakami et al., J. Exp. Med. 180: 347-352, 1994), a gene product over-expressed in 80-90% of fresh, uncultured melanomas as well as cultured melanoma cell lines (Marincola et al., J. Immunother. Emphasis Tumor Immunol. 19: 192-205, 1996) but not in other tumor or normal tissues except melanocytes. The wild-type sequences of the human DMF5 TCRs are as follows:

In some embodiments, the wild type alpha chain sequence comprises a wild type sequence as set forth in SEQ ID NO:9 of US20120071420, which is incorporated herein by reference in its entirety; D27 is in bold and uppercase:

```
                                                (SEQ ID NO: 1)
Gln Lys Glu Val Glu Gln Asn Ser Gly Pro Leu
1                5                   10

Ser Val Pro Glu Gly Ala Ile Ala Ser Leu Asn
                15                  20

Cys Thr Tyr Ser ASP Arg Gly Ser Gln Ser Phe
            25                  30

Phe Trp Tyr Arg Gln Tyr Ser Gly Lys Ser Pro
        35                  40

Glu Leu Ile Met Phe Ile Tyr Ser Asn Gly Asp
45                  50                  55

Lys Glu Asp Gly Arg Phe Thr Ala Gln Leu Asn
                60                  65

Lys Ala Ser Gln Tyr Val Ser Leu Leu Ile Arg
            70                  75

Asp Ser Gln Pro Ser Asp Ser Ala Thr Tyr Leu
        80                  85

Cys Ala Val Asn Phe Gly Gly Gly Lys Leu Ile
    90                  95

Phe Gly Gln Gly Thr Glu Leu Ser Val Lys Pro
100             105                 110

Asn Ile Gln Asn Pro Asp Pro Ala Val Tyr Gln
                115                 120

Leu Arg Asp Ser Lys Ser Ser Asp Lys Ser Val
            125                 130

Cys Leu Phe Thr Asp Phe Asp Ser Gln Thr Asn
        135                 140
```

```
Val Ser Gln Ser Lys Asp Ser Asp Val Tyr Ile
    145                 150

Thr Asp Lys Thr Val Leu Asp Met Arg Ser Met
    155                 160                 165

Asp Phe Lys Ser Asn Ser Ala Val Ala Trp Ser
                170                 175

Asn Lys Ser Asp Phe Ala Cys Ala Asn Ala Phe
                180                 185

Asn Asn Ser Ile Ile Pro Glu Asp Thr Phe Phe
                190                 195

Pro Ser Pro Glu Ser Ser Cys Asp Val Lys Leu
    200                 205

Val Glu Lys Ser Phe Glu Thr Asp Thr Asn Leu
    210                 215                 220

Asn Phe Gln Asn Leu Ser Val Ile Gly Phe Arg
                225                 230

Ile Leu Leu Leu Lys Val Ala Gly Phe Asn Leu
                235                 240

Leu Met Thr Leu Arg Leu Trp Ser Ser
    245                 250
```

In some embodiments, the wild type beta chain sequence comprises a wild type sequence as set forth in SEQ ID NO:10 of US20120071420; Leu95 is in bold and uppercase:

```
                                        SEQ ID NO: 2
Ile Ala Gly Ile Thr Gln Ala Pro Thr Ser Gln
1               5                   10

Ile Leu Ala Ala Gly Arg Arg Met Thr Leu Arg
            15                  20

Cys Thr Gln Asp Met Arg His Asn Ala Met Tyr
        25                  30

Trp Tyr Arg Gln Asp Leu Gly Leu Gly Leu Arg
        35                  40

Leu Ile His Tyr Ser Asn Thr Ala Gly Thr Thr
45                  50                  55

Gly Lys Gly Glu Val Pro Asp Gly Tyr Ser Val
                60                  65

Ser Arg Ala Asn Thr Asp Asp Phe Pro Leu Thr
                70                  75

Leu Ala Ser Ala Val Pro Ser Gln Thr Ser Val
            80                  85

Tyr Phe Cys Ala Ser Ser LEU Ser Phe Gly Thr
        90                  95

Glu Ala Phe Phe Gly Gln Gly Thr Arg Leu Thr
100                 105                 110

Val Val Glu Asp Leu Asn Lys Val Phe Pro Pro
                115                 120

Glu Val Ala Val Phe Glu Pro Ser Glu Ala Glu
                125                 130

Ile Ser His Thr Gln Lys Ala Thr Leu Val Cys
            135                 140

Leu Ala Thr Gly Phe Phe Pro Asp His Val Glu
    145                 150

Leu Ser Trp Trp Val Asn Gly Lys Glu Val His
    155                 160                 165

Ser Gly Val Ser Thr Asp Pro Gln Pro Leu Lys
            170                 175

Glu Gln Pro Ala Leu Asn Asp Ser Arg Tyr Cys
                180                 185

Leu Ser Ser Arg Leu Arg Val Ser Ala Thr Phe
            190                 195

Trp Gln Asn Pro Arg Asn His Phe Arg Cys Gln
        200                 205

Val Gln Phe Tyr Gly Leu Ser Glu Asn Asp Glu
210                 215                 220

Trp Thr Gln Asp Arg Ala Lys Pro Val Thr Gln
                225                 230

Ile Val Ser Ala Glu Ala Trp Gly Arg Ala Cys
            235                 240

Gly Phe Thr Ser Ser Tyr Gln Gln Gly Val Leu
        245                 250

Ser Ala Thr Ile Leu Tyr Glu Ile Leu Leu Gly
    255                 260

Lys Ala Thr Leu Tyr Ala Val Leu Val Ser Ala
265                 270                 275

Leu Val Leu Met Ala Met Val Lys Arg Lys Asp Phe
                280                 285
```

In some embodiments, the wild type alpha or beta chain sequence comprises a wild type sequence as set forth in Robbins et al., J. Immunol., 180: 6116-6131, 2008, which are SEQ ID NOs. 3 and 4, respectively:
DMF5 Valpha (D49 Corresponds to D27)

```
                                        (SEQ ID NO: 3)
MMKSLRVLLV ILWLQLSWVW SQQKEVEQNS GPLSVPEGAI

ASLNCTYSDR GSQSFFWYRQ YSGKSPELIM FIYSNGDKED

GRFTAQLNKA SQYVSLLIRD SQPSDSATYL CAVNFGGGKL

IFGQGTELSV KPN
```

An exemplary nucleic acid sequence encoding wild type DMF5 Valpha follows:

```
                                        (SEQ ID NO: 7)
ATGATGAAATCCTTGAGAGTTTTACTAGTGATCCTGTGGCTTCA

GTTGAGCTGGGTTTGGAGCCAACAGAAGGAGGTGGAGCAGAATT

CTGGACCCCTCAGTGTTCCAGAGGGAGCCATTGCCTCTCTCAAC

TGCACTTACAGTGACCGAGGTTCCCAGTCCTTCTTCTGGTACAG

ACAATATTCTGGGAAAAGCCCTGAGTTGATAATGTTCATATACT

CCAATGGTGACAAAGAAGATGGAAGGTTTACAGCACAGCTCAAT

AAAGCCAGCCAGTATGTTTCTCTGCTCATCAGAGACTCCCAGCC

CAGTGATTCAGCCACCTACCTCTGTGCCGTGAACTTCGGAGGAG

GAAAGCTTATCTTCGGACAGGGAACGGAGTTATCTGTGAAACCCAAT
```

DMF5 Vbeta (L114 Corresponds to L95)

```
                                        (SEQ ID NO: 4)
MRIRLLCCVA FSLLWAGPVI AGITQAPTSQ ILAAGRRMTL

RCTQDMRHNA MYWYRQDLGL GLRLIHYSNT AGTTGKGEVP
```

-continued

DGYSVSRANT DDFPLTLASA VPSQTSVYFC ASSLSFGTEA

FFGQGTRLTV V

An exemplary nucleic acid sequence encoding wild type DMF5 Vbeta follows:

(SEQ ID NO: 8)
ATGAGAATCAGGCTCCTGTGCTGTGTGGCCTTTTCTCTCCTGTGGGC

AGGTCCAGTGATTGCTGGGATCACCCAGGCACCAACATCTCAGATCC

TGGCAGCAGGACGGCGCATGACACTGAGATGTACCCAGGATATGAGA

CATAATGCCATGTACTGGTATAGACAAGATCTAGGACTGGGGCTAAG

GCTCATCCATTATTCAAATACTGCAGGTACCACTGGCAAAGGAGAAG

TCCCTGATGGTTATAGTGTCTCCAGAGCAAACACAGATGATTTCCCC

CTCACGTTGGCGTCTGCTGTACCCTCTCAGACATCTGTGTACTTCTG

TGCCAGCAGCCTAAGTTTCGGCACTGAAGCTTTCTTTGGACAAGGCA

CCAGACTCACAGTTGTA

Another exemplary sequence alpha chain sequence is shown below; D27 is in bold and upper case.

Alpha chain

LOCUS       3QEU_D                   202 aa     linear   PRI 10-OCT-2012
DEFINITION  Chain D, The Crystal Structure
Of Tcr Dmf5.
ACCESSION   3QEU_D
VERSION     3QEU_D  GI:339717586
     1      akeveqnsgp  lsvpegaias  lnctysDrgs  qsffwyrqys
            gkspelimfi  ysngdkedgr 61      ftaqlnkasq  yvsllirdsq  psdsatylca  vnfgggklif
            gqgtelsvkp  niqnpdpavy 121      qlrdskssdk  svclftdfds  qtnvsqskds  dvyitdkcvl
            dmrsmdfksn  savawsnksd 181      facanafnns  iipedtffps  pe
            (SEQ ID NO: 5)

Another exemplary sequence beta chain sequence is shown below; the amino acid corresponding to Leu95 (Leu96 in this sequence) is in bold and upper case.

Beta chain

LOCUS       3QEU_E                   243 aa     linear   PRI 10-OCT-2012
DEFINITION  Chain E, The Crystal Structure
Of Tcr Dmf5.
ACCESSION   3QEU_E
VERSION     3QEU_E  GI:339717587
     1      miagitqapt  sqilaagrrm  tlrctqdmrh  namywyrqdl
            glglrlihys  ntagttgkge 61      vpdgysysra  ntddfpltla  savpsqtsvy  fcassLsfgt
            eaffgqgtrl  tvvedlnkvf 121      ppevavfeps  eaeishtqka  tlvclatgfy  pdhvelswwv
            ngkevhsgvc  tdpqplkeqp 181      alndsryals  srlrvsatfw  gdprnhfrcq  vqfyglsend
            ewtqdrakpv  tgivsaeawg 241      rad
            (SEQ ID NO: 6)

Other sequences can include those used in Borbulevych et al., J Immunol 187:2453-2463 (2011) or Davis-Harrison et al., J Mol Biol 346: 533-550 (2005).

Provided herein are variants of the DMF5 TCR receptor that have mutations resulting in increased binding affinity. In some embodiments, a High-Affinity DMF5 Variant includes a D to Y or D to W mutation at amino acid 27 in the alpha chain (αD27Y or αD27W) and/or a L to W mutation at amino acid 95 in the beta chain (βL95W). In some embodiments, the Variant also or alternatively has one or more of an A to P mutation at amino acid 55 of the alpha chain (αA55P) and/or a T to F mutation at amino acid 102 in the beta chain (βT102F).

In some embodiments, the High-Affinity DMF5 Variant includes one or more additional mutations that do not decrease affinity. Thus, in some embodiments, the sequence can be at least 80%, 85%, 90%, 95%, or 99% identical to at least 60%, 70%, 80%, 90%, or 100% of a High-Affinity DMF5 Variant, e.g., SEQ ID NO:1 or 2; e.g., the sequence can include 1, 2, 3, 4, 5, 6, 7, 8, 9, 10, 11, 12, 13, 14, 15, 16, 17, 18, 19, or 20 mutations. In some embodiments the variant includes one or more of the following mutations described in Robbins et al., J. Immunol., 180: 6116-6131, 2008 (e.g., (3G54A); US20120071420; or Borbulevych et al. (2011) J Immunol 187 p. 2453).

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is typically at least 80% of the length of the reference sequence, and in some embodiments is at least 90% or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. In another embodiment, the percent identity of two amino acid sequences can be assessed as a function of the conservation of amino acid residues within the same family of amino acids (e.g., positive charge, negative charge, polar and uncharged, hydrophobic) at corresponding positions in both amino acid sequences (e.g., the presence of an alanine residue in place of a valine residue at a specific position in both sequences shows a high level of conservation, but the presence of an arginine residue in place of an aspartate residue at a specific position in both sequences shows a low level of conservation).

For purposes of the present invention, the comparison of sequences and determination of percent identity between two sequences can be accomplished using a BLOSUM 62 scoring matrix with a gap penalty of 12, a gap extend penalty of 4, and a frameshift gap penalty of 5.

In some embodiments, the mutation is a conservative substitution. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments (see, e.g. Table III of US2011/0201052; pages 13-15 "Biochemistry" 2nd ED. Stryer ed (Stanford University); Henikoff et al., PNAS 1992 Vol 89 10915-10919; Lei et al., J Biol Chem 1995 May 19; 270(20):11882-6).

Therapeutic Compositions and Imaging Reagents

Also described herein are compounds that include one or more non-TCR moieties in addition to the High-Affinity DMF5 Variants described herein, e.g., linked to the N or C terminus of the High-Affinity DMF5 Variant (preferably the C terminus), or internally, e.g., linked to an internal cysteine, so long as the binding activity of the variant is not affected. In some embodiments, the non-TCR moiety is a therapeutic agent or a detectable moiety. These compounds can be used to treat and/or detect cancers, i.e., MART-1 expressing cancers, including melanoma, e.g., malignant melanomas, including primary cutaneous malignant melanomas and mucosal melanomas; and other tumors of melanocytic origin or differentiation (i.e., melanosome producing), e.g., clear cell sarcoma, melanotic neurofibroma, melanotic schwannoma and other melanotic neural crest derived tumors, as well as perivascular epitheloid cell tumors, angiomyolipoma, lymphangioleiomyoma/tosis), and pulmonary sugar tumors. In preferred embodiments, the cancer is melanoma, e.g., melanoma with HLA-A201 tissue type. Methods for diagnosing a subject with a MART-1 expressing cancer are known in the art, and can include obtaining a sample comprising one or more cells of the cancer or tumor (e.g., cells that are known or suspected to be cancerous or from a tumor) and detecting expression of MART-1 in the cells, using methods know in the art (e.g., methods that detect the presence of MART-1 mRNA (GenBank Acc. No. NM_005511.1) or protein (GenBank Acc. No. NP_005502.1), e.g., PCR-based or antibody based methods).

Therapeutic Compositions

In some embodiments, the invention provides therapeutic compositions in which the High-Affinity DMF5 Variants described herein are linked to one or more anti-cancer therapeutic agents, i.e., agents that have a therapeutic effect against cancer, e.g., against melanoma. In some embodiments, the therapeutic effect is an anti-tumor effect, e.g., resulting in cancer cell death or stasis, tumor regression or shrinkage, reduction or delay in tumor growth, or a reduction or delay in tumor metastasis.

The High-Affinity DMF5 Variant as described herein can be used to deliver a variety of anti-cancer therapeutic agents, e.g., a radioisotope; an anticancer drug such as a genotoxin; or any other cytotoxic moiety, e.g., molecules of plant, fungal, or bacterial origin, or biological proteins (e.g., protein toxins) or particles (e.g., a recombinant viral particles, e.g., via a viral coat protein), or mixtures thereof. The therapeutic agent can be an intracellularly active drug or other agent, such as short-range radiation emitters, including, for example, short-range, high-energy α-emitters, as described herein. In some embodiments, the High-Affinity DMF5 Variant can be coupled to a molecule of plant or bacterial origin (or derivative thereof), e.g., a maytansinoid (e.g., maytansinol or the DM1 maytansinoid). DM1 is a sulfhydryl-containing derivative of maytansine that can be linked to the peptide, e.g., via a disulfide linker that releases DM1 when inside target cells. The disulfide linkers display greater stability in storage and in serum than other linkers. Maytansine is a cytotoxic agent that effects cell killing by preventing the formation of microtubules and depolymerization of extant microtubules. It is 100- to 1000-fold more cytotoxic than anticancer agents such as doxorubicin, methotrexate, and vinca alkyloid, which are currently in clinical use. Alternatively, the High-Affinity DMF5 Variant as described herein can be coupled to a taxane, a calicheamicin, a proteosome inhibitor, or a topoisomerase inhibitor. [(1R)-3-methyl-1-[[(2S)-1-oxo-3-phenyl-2-[(3-mercaptoacetyl)amino]propyl]amino]butyl]Boronic acid is a suitable proteosome inhibitor. N,N'-bis[2-(9-methylphenazine-1-carboxamido)ethyl]-1,2-ethanediamine is a suitable topoisomerase inhibitor.

Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and enomycin. In some embodiments, the High-Affinity DMF5 Variant is conjugated to maytansinoids, e.g., maytansinol (see U.S. Pat. No. 5,208,020), CC-1065 (see U.S. Pat. Nos. 5,475,092, 5,585, 499, 5,846,545). Procedures for preparing enzymatically active polypeptides of the immunotoxins are described in WO84/03508 and WO85/03508, which are hereby incorporated by reference. Examples of cytotoxic moieties that can be conjugated to the antibodies include adriamycin, chlorambucil, daunomycin, methotrexate, neocarzinostatin, and platinum.

To kill or ablate cancerous cells, a High-Affinity DMF5 Variant can be conjugated with a prodrug that is activated only when in close proximity with a prodrug activator. The prodrug activator is conjugated with a second High-Affinity DMF5 Variant, e.g., a second High-Affinity DMF5 Variant according to the present invention, preferably one that binds to a non-competing site on the same receptor (e.g., plectin-1) or cell. Whether two High-Affinity DMF5 Variant bind to competing or non-competing binding sites can be determined by conventional competitive binding assays. Drug-prodrug pairs suitable for use are known in the art, see, e.g., in Blakely et al., Cancer Research 56:3287-3292 (1996).

A drug attached to a variant as described herein can also include agents that are derived from, or that beneficially modulate host biological processes, such as interferons, tumor growth factors, tumor necrosis factors, growth factors such as GM-CSF and G-CSF and interleukins, for example, interleukin-2, interleukin-6, interleukin-7 and interleukin-12, and the like. An drug attached to a peptide of the present invention may comprise an agent which damages DNA and/or prevent cells from multiplying, such as genotoxins. A genotoxin includes but is not limited to alkylating agents, antimetabolites, DNA cutters, DNA binders, topoisomerase poisons and spindle poisons. Examples of alkylating agents are lomustine, carmustine, streptozocin, mechlorethamine, melphalan, uracil nitrogen mustard, chlorambucil, cyclosphamide, iphosphamide, cisplatin, carboplatin, mitomycin, thiotepa, dacarbazin, procarbazine, hexamethyl melamine, triethylene melamine, busulfan, pipobroman, mitotane and other platine derivatives.

Alternatively, the High-Affinity DMF5 Variant can be coupled to high energy radiation emitters, for example, a radioisotope, such as $^{131}$I, a γ-emitter, which, when localized at the tumor site, results in a killing of several cell diameters. See, e.g., Order, "Analysis, Results, and Future Prospective of the Therapeutic Use of Radiolabeled Antibody in Cancer Therapy", in *Monoclonal Antibodies for Cancer Detection and Therapy*, R. W. Baldwin et al. (eds.), pp 303-316 (Academic Press 1985). Other suitable radioisotopes include α-emitters, such as $^{212}$Bi, $^{213}$Bi, and $^{211}$At, and β-emitters, such as $^{186}$Re and $^{90}$Y. Lu$^{117}$ may also be used as both an imaging and cytotoxic agent.

Radioimmunotherapy (RIT) using High-Affinity DMF5 Variant labeled with $^{131}$I, $^{90}$Y, and $^{177}$Lu can also be used. There are significant differences in the physical characteristics of these three nuclides and as a result, the choice of radionuclide can be important in order to deliver maximum radiation dose to the tumor. The higher beta energy particles of $^{90}$Y may be good for bulky tumors, but it may not be necessary for small tumors and especially bone metastases, (e.g. those common to prostate cancer). The relatively low energy beta particles of $^{131}$I are ideal, but in vivo dehalogenation of radioiodinated molecules is a major disadvantage for internalizing High-Affinity DMF5 Variants. In contrast, $^{177}$Lu has low energy beta particle with only 0.2-0.3 mm range and delivers much lower radiation dose to bone marrow compared to $^{90}$Y. In addition, due to longer physical half-life (compared to $^{90}$Y), the tumor residence times are higher. As a result, higher activities (more mCi amounts) of $^{177}$Lu labeled agents can be administered with comparatively less radiation dose to marrow. There have been several clinical studies investigating the use of $^{177}$Lu labeled antibodies in the treatment of various cancers (see, e.g., Mulligan et al., Clin Cancer Res. 1: 1447-1454 (1995); Meredith et al., Nucl Med 37:1491-1496 (1996); Alvarez et al., Gynecologic Oncology 65: 94-101 (1997)).

The High-Affinity DMF5 Variant can also be conjugated or fused to viral surface proteins present on viral particles. For example, a High-Affinity DMF5 Variant could be fused (e.g., to form a fusion protein) to a viral surface protein. Alternatively, a High-Affinity DMF5 Variant could be chemically conjugated (e.g., via a chemical linker) to a viral surface protein. Preferably, the virus is one that fuses with endocytic membranes, e.g., an influenza virus, such that the virus is internalized along with the High-Affinity DMF5 Variant and thereby enters and kills cancer cells. The virus can be genetically engineered as a cellular toxin. For example, the virus could express or induce the expression of genes that are toxic to cells, e.g., cell death promoting genes. Preferably, such viruses would be incapable of viral replication.

Additional examples of cytotoxic peptides or proteins include Idarubicin; CRM9 (e.g., FN18-CRM9, Knechtle et al., Transplantation 1997; 63:1-6); or pokeweed antiviral protein. In some embodiments, the cytotoxic protein is a bacterial toxin, e.g., diphtheria toxin (DT) or portions or variants thereof, e.g., Met1-Thr387, e.g., as described in Aullo et al., EMBO J. 11(2):575-83 (1992); Abi-Habib et al., Blood. 104(7):2143-2148 (2004); Perentesis et al., Proc. Natl. Acad. Sci. USA 85:8386-8390 (1988); Zettlemeissl et al., Gene. 41(1):103-111 (1986); US 2009/0010966; US20090041797; U.S. Pat. No. 5,843,711; U.S. Pat. No. 7,585,942; U.S. Pat. No. 7,696,338; or US20080166375; or *Pseudomonas* exotoxin (PE), or portions or variants thereof, e.g., as described in U.S. Pat. Nos. 4,545,985; 4,892,827; 5,458,878; 7,314,632; Song et al., Protein Expression and Purification 44(1):52-57 (2005); Theuer et al., J. Biol. Chem. 267(24):16872-16877 (1992); Heimbrook et al., Proc Natl Acad Sci USA. 87(12):4697-4701 (1990); Debinski et al., Mol Cell Biol. 11(3):1751-1753 (1991); Chaudhary et al., Proc. Nadl. Acad. Sci. USA 87:308-312 (1990). In some embodiments, the cytotoxic protein is a plant toxin, e.g., a plant holotoxin (e.g., class II ribosome-inactivating proteins such as ricin (e.g., deglycosylated ricin A chain (dgA)), abrin, mistletoe lectin, or modeccin) or hemitoxin (class I ribosome-inactivating proteins, e.g., PAP, saporin, bryodin 1, bouganin, or gelonin), or fragments or variants thereof that retain cytotoxic activity. See, e.g., Neville et al., J Contr Rel 1993; 24:133-141; Vallera, Blood 1994; 83:309-317; Vitetta et al., Immunology Today 1993; 14:252-259; Kreitman et al., AAPS Journal. 2006; 8(3):E532-E551). Suitable sequences are known in the art.

Imaging Reagents

In some embodiments, the invention provides compounds that are useful as imaging reagents in which the non-TCR moiety is a detectable moiety, e.g., a radioactive moiety (e.g., $^{35}$S, $^{32}$P, $^{3}$H, or $^{14}$C), a chemiluminescent moiety (e.g., Streptavidin-Alkaline Phosphatase, Streptavidin-Horseradish Peroxidase, Streptavidin-Biotinylated Horseradish Peroxidase, e.g., for detection with ECL™ or a variant thereof (Amersham Biosciences, Piscataway, N.J.)), a fluorescent moiety (e.g., CyDyes (such as Cy3, Cy3B, Cy3.5, Cy5, Cy5.5, Cy7, Cy5Q, Cy7Q, Cy2-Streptavidin, Cy3-Streptavidin, Cy5-Streptavidin, Streptavidin-Fluorescein, Streptavidin-Texas Red (Amersham Biosciences, Piscataway, N.J.), fluorescein, rhodamine, Texas red, cyanine, Cascade Blue, or phycoerythrin), quantum dots (see, e.g., Watson et al., BioTechniques 2003 February; 34(2):296-300, 302-3; Goldman et al., J. Am. Chem. Soc. 2002 Jun. 5; 124(22):6378-82; Han et al., Nat. Biotechnol. 2001 July; 19(7):631-5; Chan et al., Science 1998 Sep. 25; 281(5385):2016-8), or other directly or indirectly detectable moiety (e.g., gold or other particles). Contrast agents, e.g., contrast agents for MRI or NMR, for X-ray CT, Raman imaging, optical coherence tomography, absorption imaging, ultrasound imaging, or thermal imaging can be used. Exemplary contrast agents include gold (e.g., gold nanoparticles), gadolinium (e.g., chelated Gd), iron oxides (e.g., superparamagnetic iron oxide (SPIO), monocrystalline iron oxide nanoparticles (MIONs), and ultrasmall superparamagnetic iron oxide (USPIO)), manganese chelates (e.g., Mn-DPDP), barium sulfate, iodinated contrast media (iohexyl), microbubbles, or perfluorocarbons. In a preferred embodiment, the variant is coupled to a paramagnetic agent, e.g., a paramagnetic nanoparticle, e.g., cross-linked iron oxide (CLIO) nanoparticles; see, e.g., US 20110046004; Josephson et al., Bioconjug. Chem., 10(2):186-91 (1999).

In some embodiments, the detectable moiety can be or include a fluorophore, e.g., a near infrared fluorophore (NIRF). A number of NIRFs useful in the methods and compositions described herein are known in the art, e.g., including Cy5.5, Cy5 and Cy7 (Amersham, Arlington Hts., IL; IRD41 and IRD700 (LI-COR, Lincoln, Nebr.); NIR-1, (Dejindo, Kumamoto, Japan); LaJolla Blue (Diatron, Miami, Fla.); indocyanine green (ICG) and its analogs (Licha et al., 1996, SPIE 2927:192-198; Ito et al., U.S. Pat. No. 5,968,479); indotricarbocyanine (ITC; WO 98/47538); and chelated lanthanide compounds. Fluorescent lanthanide metals include europium and terbium. Fluorescence properties of lanthanides are described in Lackowicz, 1999, Principles of Fluorescence Spectroscopy, 2$^{nd}$ Ed., Kluwar Academic, New York. The fluorophores can be covalently linked to the plectin-1 binding moiety, or to a nanoparticle, e.g., via a fluorochrome attachment moiety, backbone, or spacer using any suitable reactive group on the fluorochrome and a compatible functional group on the fluorochrome attachment moiety, backbone, or spacer. For example, a carboxyl group (or activated ester) on a fluorochrome can be used to form an amide linkage with a primary amine such as the epsilon-amino group of the lysyl side chain on polylysine. Alternatively or in addition, the fluorophores can be linked directly to the backbone or linked to the backbone through nonbiodegradable spacers. See, e.g., US P.G.Pub. 20060275775.

The High-Affinity DMF5 Variants can be linked to the detectable moieties directly, e.g., as a fusion protein with protein or peptide detectable moieties (with or without an optional linking sequence, e.g., a flexible linker sequence) or via a chemical coupling moiety. A number of such coupling moieties are known in the art, e.g., a peptide linker or a chemical linker, e.g., as described in International Patent Application Publication No. WO 2009/036092.

These moieties can be detected using methods known in the art. For example, a number of methods are known in the art for detection of fluorescent moieties, including, but not limited to, fluorescence polarization (FP), fluorescence resonance energy transfer (FRET), time-resolved fluorescence resonance energy transfer (TR-FRET), and fluorescence intensity (FI).

Nucleic Acids, Expression Vectors, and Host Cells

Also provided herein are polynucleotides (also referred to herein as nucleic acids) that encode a high-affinity variant as described herein, as well as vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a nucleic acid that encodes a high-affinity variant as described herein in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce a high-affinity variant as described herein, including fusion proteins as described herein.

The recombinant expression vectors of the invention can be designed for expression of a high-affinity variant as described herein in prokaryotic or eukaryotic cells. For example, polypeptides of the invention can be expressed in $E.$ $coli$, insect cells (e.g., using baculovirus expression vectors), yeast cells or mammalian cells. Suitable host cells are discussed further in Goeddel, (1990) $Gene\ Expression$ $Technology:\ Methods\ in\ Enzymology$ 185, Academic Press, San Diego, Calif. Alternatively, the recombinant expression vector can be transcribed and translated in vitro, e.g., using T7 promoter regulatory sequences and T7 polymerase.

Expression of proteins in prokaryotes is most often carried out in $E.\ coli$ with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) $Gene$ 67:31-40), pMAL (New England Biolabs, Beverly, Mass.) and pRIT5 (Pharmacia, Piscataway, N.J.), which fuse glutathione S-transferase (GST), maltose E binding protein, or protein A, respectively, to the target recombinant protein.

The expression vector can be, e.g., a yeast expression vector, a vector for expression in insect cells (e.g., a baculovirus expression vector), or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the lymphoid-specific promoters (Calame and Eaton (1988) Adv. Immunol. 43:235-275), in particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748).

In some embodiments, the vector is pMSGV1, which is derived from pMSGV and includes a murine stem cell virus long terminal repeat containing an extended gag region and Kozak sequence (Hughes et al., Hum Gene Ther. 2005; 16:457-472). In some embodiments, the vector is pMSGV DMF5 furin 2-A, which was generated by introducing DMF5 TCR-α cDNA15 followed by a furin T2A cleavage sequence and DMF5 TCR-β, as described in Johnson et al., 2006, supra, and Johnson et al., Blood. 114: 535-546, 2009.

Another aspect the invention provides a host cell which includes a nucleic acid molecule described herein, e.g., a nucleic acid molecule encoding a high-affinity variant as described herein within a recombinant expression vector or a nucleic acid molecule containing sequences that allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a high-affinity variant as described herein can be expressed in bacterial cells such as *E. coli*, insect cells, yeast or mammalian cells (e.g., Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a high-affinity variant as described herein. Accordingly, the invention further provides methods for producing a high-affinity variant as described herein using the host cells of the invention. In one embodiment, the method includes culturing the host cell of the invention (into which a recombinant expression vector encoding a high-affinity variant as described herein has been introduced) in a suitable medium such that a high-affinity variant as described herein is produced. In another embodiment, the method further includes isolating a high-affinity variant as described herein from the medium or the host cell.

Also provided herein are human cells, e.g., hematopoietic cells, e.g., human PBLs, transformed with a nucleic acid that encodes a high-affinity variant as described herein.

Gene Therapy

The nucleic acids encoding a high-affinity variant described herein can be incorporated into a nucleic acid construct to be used as a part of a nucleic acid therapy protocol. Thus described herein are targeted expression vectors for in vivo or in vitro transfection and expression of a polynucleotide that encodes a high-affinity variant as described herein, in particular cell types, especially autologous peripheral blood lymphocytes (PBLs), and methods of use thereof. Expression constructs of such components can be administered in any effective carrier, e.g., any formulation or composition capable of effectively delivering the polynucleotide that encodes a high-affinity variant as described herein to cells in vivo or in vitro. Approaches include insertion of the polynucleotide that encodes a high-affinity variant as described herein in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized (e.g., antibody conjugated), polylysine conjugates, gramacidin S, artificial viral envelopes or other such intracellular carriers, as well as direct injection of the nucleic acid construct or $CaPO_4$ precipitation carried out in vivo. RNA (e.g., RNA encoding the variant) can also be delivered directly to the cell, e.g., using electroporation.

A preferred approach for in vivo introduction of nucleic acid into a cell is by use of a viral vector containing nucleic acid, e.g., a cDNA that encodes a high-affinity variant as described herein. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant nucleic acid delivery system for the transfer of exogenous nucleic acids in vivo or in vitro, particularly into humans. These vectors provide efficient delivery of nucleic acids into cells, and the transferred nucleic acids are stably integrated into the chromosomal DNA of the host. The development of specialized cell lines (termed "packaging cells") which produce only replication-defective retroviruses has increased the utility of retroviruses for nucleic acid therapy, and defective retroviruses are characterized for use in nucleic acid transfer for gene therapy purposes (for a review see Miller, *Blood* 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., *Current Protocols in Molecular Biology*, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of nucleic acids into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral nucleic acid delivery system useful in the present methods utilizes adenovirus-derived vectors. The genome of an adenovirus can be manipulated, such that it encodes and expresses a protein or gene product of interest but is inactivated in terms of its ability to replicate in a normal lytic viral life cycle. See, for example, Berkner et al., BioTechniques 6:616 (1988); Rosenfeld et al., Science 252: 431-434 (1991); and Rosenfeld et al., Cell 68:143-155 (1992). Suitable adenoviral vectors derived from the adenovirus strain Ad type 5 dl324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other nucleic acid delivery vectors (Berkner et al., supra; Haj-Ahmand and Graham, J. Virol. 57:267 (1986).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993)).

In addition to viral transfer methods, such as those illustrated above, non-viral methods can also be employed to cause expression of a nucleic acid compound described herein (e.g., a polynucleotide that encodes a high-affinity variant as described herein) in a cell or tissue of a subject. Typically non-viral methods of nucleic acid transfer rely on the normal mechanisms used by mammalian cells for the uptake and intracellular transport of macromolecules. In some embodiments, non-viral nucleic acid delivery systems can rely on endocytic pathways for the uptake of the subject nucleic acid by the targeted cell. Exemplary nucleic acid delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22): 1896-905 (2000); or Tam et al., Gene Ther. 7(21):1867-74 (2000).

In some embodiments, a polynucleotide that encodes a high-affinity variant as described herein is entrapped in liposomes bearing positive charges on their surface (e.g., lipofectins), which can be tagged with antibodies against cell surface antigens of the target tissue (Mizuno et al., No Shinkei Geka 20:547-551 (1992); PCT publication WO91/06309; Japanese patent application 1047381; and European patent publication EP-A-43075).

In clinical settings, the nucleic acid delivery systems for the polynucleotide that encodes a high-affinity variant as described herein can be introduced into a cell or subject by any of a number of methods, each of which is familiar in the art. For instance, a pharmaceutical preparation of the nucleic acid delivery system can be introduced systemically, e.g., by intravenous injection, and specific transduction of the protein in the target cells will occur predominantly from specificity of transfection, provided by the nucleic acid delivery vehicle, cell-type or tissue-type expression due to the transcriptional regulatory sequences controlling expression of the receptor nucleic acid, or a combination thereof. In other embodiments, initial delivery of the recombinant nucleic acidis more limited, with introduction into the subject being quite localized. For example, the nucleic acid delivery vehicle can be introduced by catheter (see U.S. Pat. No. 5,328,470) or by stereotactic injection (e.g., Chen et al., PNAS USA 91: 3054-3057 (1994)).

A pharmaceutical preparation of can consist essentially of a nucleic acid delivery system in an acceptable diluent, or can comprise a slow release matrix in which the nucleic acid delivery vehicle is embedded. Alternatively, where the complete nucleic acid delivery system can be produced intact from recombinant cells, e.g., retroviral vectors, the pharmaceutical preparation can comprise one or more cells, which produce the nucleic acid delivery system.

Pharmaceutical Compositions and Methods of Administration

The methods described herein include the manufacture and use of pharmaceutical compositions, which include the High Affinity Variants described herein as active agents. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy*, 21st ed., 2005; and the books in the series *Drugs and the Pharmaceutical Sciences: a Series of Textbooks and Monographs* (Dekker, NY). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

The compositions described herein can also be administered orally, by inhalation, or topically.

Therapeutic compounds that are or include nucleic acids can be administered by any method suitable for administration of nucleic acid agents, such as a DNA vaccine.

These methods include gene guns, bio injectors, and skin patches as well as needle-free methods such as the microparticle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid.

Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser together with instructions for administration.

Methods of Use

The High-Affinity DMF5 Variants described herein can be used, e.g., to treat or detect cancer, e.g., melanoma, in a subject. As used in this context, to "treat" means to ameliorate at least one symptom of the cancer. Administration of a therapeutically effective amount of a high-affinity variant as described herein for the treatment of melanoma will result in one or more of cancer cell death or stasis, tumor regression or shrinkage, reduction or delay in tumor growth, or a reduction or delay in cancer metastasis. The methods of treatment can include administering a composition comprising a High-Affinity DMF5 Variant as described herein, e.g., with or without a therapeutic agent or a detectable moiety, to a subject who is in need of, or who has been determined to be in need of, such treatment.

In some embodiments, the methods of treatment include administering to the subject (i.e., a subject who has cancer, e.g., melanoma) T cells (preferably autologous T cells) that have been genetically engineered to express a high-affinity variant as described herein. Methods for doing so are known in the art, see, e.g., Johnson et al. 2009. Blood. 114: 535-546; Morgan et al., 2006. Science. 314: 126-129; Borbulevych et al., J. Immunol. 2011 Sep. 1; 187(5): 2453-2463. In some embodiments, the methods include obtaining cells, preferably PBLs, from a human, preferably from the subject who is to be treated (i.e., autologous cells). The cells are transfected with a vector comprising a nucleic acid encoding a high-affinity variant as described herein, and maintained in culture, optionally for a time sufficient for expansion to occur. Expression of the high-affinity variant as described herein can be optionally confirmed using methods known in the art, e.g., tetramer staining and flow cytometric analysis, and cell function can also be evaluated, e.g., by overnight coculture with cognate antigen-bearing target cells ($1\times10^5$: $1\times10^5$) and enzyme-linked immunosorbent assay (ELISA) measurement (Pierce Endogen) of interferon-γ (IFN-γ) produced in the culture supernatant. The cells are then administered to the subject, e.g., by infusion into the subject intravenously.

The methods of use can also include imaging methods. In these methods, an imaging reagent comprising a high-affinity variant as described herein linked to a detectable moiety is administered to the subject, and an appropriate method is used to detect localization of the moiety in the subject's body. For example, MRI or NMR, for X-ray CT, Raman imaging, optical coherence tomography, absorption imaging, ultrasound imaging, or thermal imaging can be used when a high-affinity variant linked to an appropriate detectable moiety, i.e., an appropriate contrast agent, is used.

Imaging methods can also be carried out in vitro. For example, one other potential use is imaging to detect antigen-expressing cells in a T cell population that might be cultured from a patient. For example, the T cells are removed, grown up, and the high affinity variant, coupled to a detectable moiety, e.g., a fluorescent tag, is used to identify T cells expressing target antigen, e.g., using flow cytometry/FACS.

EXAMPLES

The invention is further described in the following examples, which do not limit the scope of the invention described in the claims.

Example 1

Evidence for a Dynamically Driven T Cell Signaling Mechanism

Oligomerization, stronger associations with neighboring subunits, and conformational changes can all be facilitated by changes in molecular flexibility. Global reductions in flexibility can help overcome the entropy barrier associated with binding and enhance complementarity at interfaces (6).

More defined conformational changes that occur upon binding often take place at regions with heightened intrinsic flexibility (7). Recent work in a number of systems has demonstrated how ligand binding can alter protein flexibility across time and length scales, impacting binding behavior at distant sites in the absence of crystallographically-observed structural changes (8-10). This process, termed dynamically-driven allostery, has attracted attention as a unifying mechanism for the general phenomenon of allostery and is of particular interest in cases where signaling occurs in the absence of clear structural changes (reviewed in ref 11).

As large conformational changes that could communicate pMHC binding have not been observed in the TCR, we wished to explore the potential for alterations in protein flexibility as a mechanism to communicate receptor engagement.

Materials and Methods

The following materials and methods were used in Example 1.

Protein Expression and Purification

Recombinant A6, DMF5, and HLA-A2 were refolded from inclusion bodies and purified as described previously (12). Constructs were stabilized either with an engineered disulfide bond (13) or a C-terminal leucine zipper (14). Synthetic peptide was purchased from Genscript.

Hydrogen/Deuterium Exchange

Exchange was initiated by diluting samples in at 25° C. in 25 mM HEPES, 50 mM NaCl, pH 7.4 10-fold with the same buffer made with 99.9% $^2H_2O$. For analysis of free A6, DMF5, and Tax/HLA-A2, protein concentration after dilution was 10 μM. For analysis of bound A6, concentrations after dilution were 10 μM TCR, 40 μM pMHC, resulting in 94% occupancy. These concentrations were reversed for analysis of bound Tax/HLA-A2. For examining DMF5, concentrations after dilution were 20 μM TCR and 80 μM pMHC, resulting in 100% occupancy. For A6 with non-cognate MART-1$_{26-35}$/HLA-A2, concentrations after dilution were 10 μM TCR and 45 μM pMHC. After dilution into $^2H_2O$, 5 μL aliquots were removed at time points ranging from five seconds to 10 hours. For each aliquot, exchange was quenched at 0° C. with 100 μL of 0.1% trifluoracetic acid at pH 2.4, conditions under which the rate of hydrogen/deuterium exchange is minimal (15). Pepsin (8 μL at 1 mg/mL) was added and digestion performed for 5 minutes before freezing in liquid nitrogen. Samples were stored at −80° C. until analysis.

Identification of Peptic Fragments of TCR and HLA-A2

Peptic fragments were identified by LC/MS/MS. 500 ng of the pepsin digest was loaded onto a 75 μm×15 cm C12 column. Peptides were eluted using an Eksigent nano UltraLC into the nanospray source of an AB Sciex 5500 QTrap spectrometer. An individual survey scan was performed and up to six dependent MS/MS acquisitions were collected every cycle. Data were searched using the Paragon algorithm in thorough search mode with no enzyme specificity (16). The sequences of the TCR, HLA-A2, β$_2$m, and potential contaminants (keratins, pepsin, and the E. coli genome) were searched. False detection rates were determined using a decoy-database strategy (17). In all cases, the relevant proteins were the top hit and all peptides passed on for further analysis identified at a 99% CI.

MALDI Mass Spectrometry

A matrix solution of 2,5-dihydroxybenzoic acid in 50:50 0.1% trifluoroacetic acid (pH 2.4) and acetonitrile was prepared and mixed 1:1 with the acidified protein on a chilled MALDI target. The target was dried under vacuum to minimize back exchange; experiments in which fully deuterated fragments were processed the same way indicated back exchange never exceeded 5%. Spectra were acquired on a Bruker Autoflex III Smartbeam MALDI-TOF mass spectrometer. The instrument was calibrated with a standard peptide mixture prior to collection of each dataset.

MALDI Data Processing

The centroid (mass weighted average) of the isotopic envelope for each peptide was calculated via a spreadsheet after data export. The level of backbone deuterium incorporation for each peptide was calculated as:

$$\% \text{ deuteration} = 100 \times \frac{(m) - m_{0\%}}{m_{100\%} - m_{0\%}}$$

where <m> is the centroid mass, $m_{0\%}$ is the mass of the undeuterated sample, and $m_{100\%}$ is the mass of the peptide in which the backbone is fully deuterated. In all cases examined, exchange was complete by 10 minutes as shown in FIG. 1B; thus percent deuteration at 10 minutes was used for comparisons.

Surface Plasmon Resonance

Surface plasmon resonance experiments with the wild-type and high affinity variant of DMF5 were performed using a steady state assay with a Biacore 3000 instrument as previously described (12). Solution conditions were 10 mM HEPES, 150 mM NaCl, 3 mM EDTA, 0.005% surfactant P-20, pH 7.4, 25° C.

Anisotropic Network Model Calculations

Anisotropic Network Model calculations were performed using the Anisotropic Network Model server with a cutoff for interactions between α carbon atoms of 15 Å and a distance weight for interactions between α carbon atoms of 2.5 (18). Calculations were performed on the separately solved structures of A6 and its complex with pMHC (14, 19).

Structure-based Computational Design of a High Affinity DMF5 Variant

Design of the high affinity DMF5 variant was performed using the ZAFFI algorithm (20) and the structure of wild-type DMF5 in complex with the decameric MART-1 epitope (21). Briefly, mutations were simulated using the interface protocol of Rosetta 2.3 (22), using gradient-based minimization to refine backbone and torsion angles and rigid-body position before and after mutation (this was superior for reproducing binding affinities compared to the fixed backbone protocol used originally). From this analysis, the threshold of the ZAFFI filter function was raised to 0.3. Computational mutagenesis of 31 DMF5 residues resulted in 589 mutants. Ten of the highest scoring mutants were evaluated experimentally, and two that led to enhanced binding (αD27Y, βL95W) combined to generate the high affinity variant.

Results and Discussion

Ligation by pMHC Globally Rigidifies the A6 TCR

Although NMR remains the most powerful method for investigating protein motions, complications resulting from the size, complexity, and stability of TCRs and their complexes have limited NMR studies of TCR-pMHC interactions, requiring the use of simplified systems (23). To circumvent these challenges, we utilized hydrogen/deuterium exchange monitored by proteolysis and mass spectrometry (HDX-MS) as a tool to probe flexibility (reviewed in ref. 24). In HDX-MS, protein prepared in aqueous solution is incubated in $^2H_2O$, digested into fragments, and backbone deuteron incorporation for each fragment determined via mass spectrometry. Increased levels of deuteron incorporation indicate that backbone amides become more accessible to exchange though greater sampling of more open, solvent-exposed states, while lower levels of incorporation indicate that amides are protected from exchange through less frequent excursions into solvent exposed states. HDX-MS has been utilized in a number of cases to explore protein motions and their changes, and has been particularly useful in characterizing low-frequency motions in samples not easily adaptable to NMR (24).

Figure 1C:
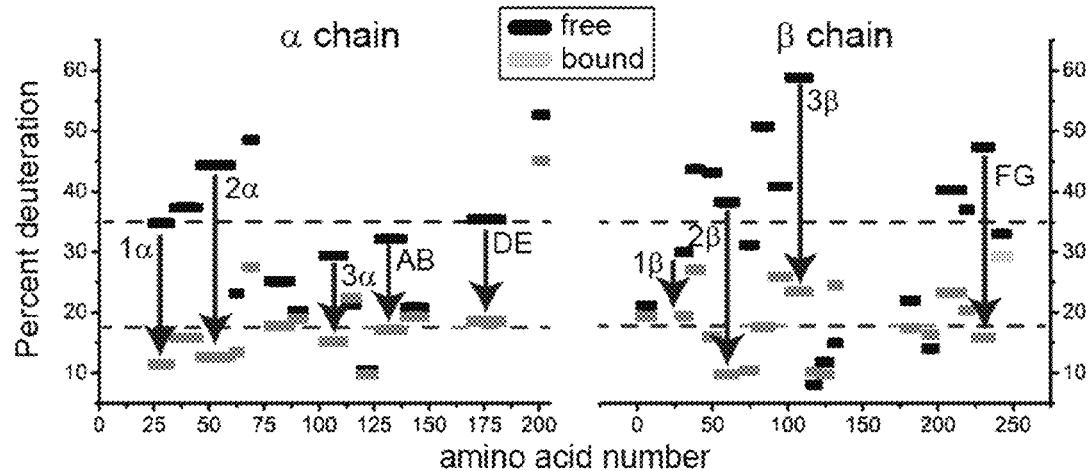

We began by performing HDX-MS on the ectodomain of the well-characterized A6 TCR in the absence and presence of its cognate pMHC ligand, the Tax peptide presented by the class I MHC HLA-A*0201 (HLA-A2). The A6 TCR is particularly amenable to this analysis, as its high affinity towards Tax/HLA-A2 allows full receptor occupancy to be achieved without requiring concentrations of pMHC that would hinder detection of TCR signals in the analysis of the exchange reactions (12). As shown in FIG. 1A, the A6 TCR showed decreased levels of deuteration upon ligation. Data for each peptide fragment were collected as a function of time out to several hours, but in all cases examined, exchange was essentially complete within 10 minutes as shown in FIG. 1B. The average deuteration of the free TCR after 10 minutes of exchange was 35%, whereas in the complex the average deuteration after 10 minutes of exchange was 18% (FIG. 1C). These values were reproducible, with a repeat experiment yielding free and bound levels of 34% and 16%, respectively. As shown in FIG. 1C, the reduced deuteration was distributed across the TCR, indicating that TCR ligation results in a global reduction in structural fluctuations, extending from the variable to the constant domains, although the extent varies throughout the molecule. Similar global reductions in flexibility upon ligand binding have been seen in other protein systems, such as the DNA binding protein BirA (25).

As expected, peptide fragments covering the A6 CDR loops showed reduced deuteration. Beyond the CDR loops, reduced deuteration was also seen for other key regions of the TCR, including a more than three-fold reduction in deuteration for a fragment spanning the β chain FG loop, a prominent structural feature that forms part of a cavity that has been proposed as a docking site for CD3εγ (26). A molecular dynamics simulation has shown that the CD3εδ subunit also rigidifies upon binding (in this case a monoclonal antibody) (27). It is not known if CD3εγ likewise rigidifies upon ligand binding; however, stronger binding of one or both of the CD3ε subunits to the TCR resulting from pMHC-induced rigidification could play a role in T cell triggering.

Although the FG loop is the most prominent feature impacted in the TCR constant domains, the reduction in flexibility includes other elements also implicated in either TCR oligomerization or interactions with CD3 subunits. This includes the α chain AB loop, which has been suggested to play a role in mediating interactions between adjacent TCRs on T cell membranes (3). Reduced AB loop flexibility could underlie a prior observation of a conformational change occurring upon TCR ligation (4), which is observed to a small extent when comparing the bound and free structures of A6 (19).

The ectodomain of the A6 TCR utilized for the data in FIG. 1 included an engineered disulfide bond near the base of the TCR constant domains to ensure heterodimer stability and facilitate proper chain pairing during protein refolding (13). An experiment with an alternate construct stabilized instead by a C-terminal heterodimeric coiled coil (14) also showed reduced deuteration upon binding at regions distant from the antigen binding site, indicating that the results in FIG. 1 are not a consequence of the method used to stabilize the receptor. A control experiment in which HDX-MS was performed with A6 before and after mixing with non-cognate ligand did not show reduced deuteration.

Ligation by pMHC Globally Rigidifies the DMF5 TCR

Figure 2A:
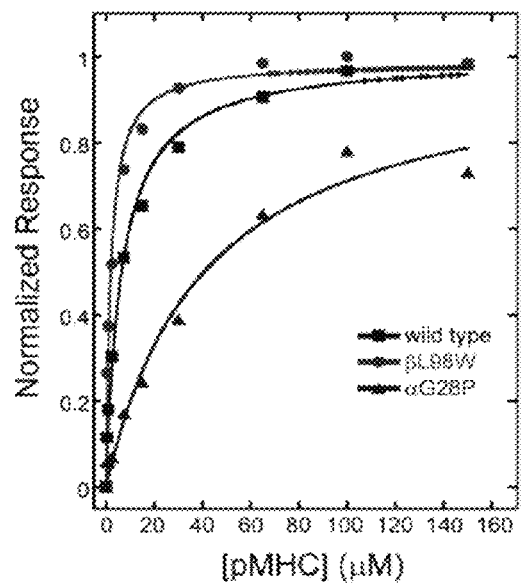
FIGS. 2A-C. The DMF5 TCR also undergoes a global reduction in flexibility upon pMHC binding. (A) Steady-state binding equilibrium data for ELA/HLA-A2 binding wild type DMF5 and βL95W and αG29P mutants. Solid lines represent a fit to a 1:1 equilibrium binding model. (B) Kinetic titration data for ELA/HLA-A2 binding of the high affinity YW (αD26Y/βL98W) mutant of DMF5. Data are in black in the bottom panel; the grey line is a fit to a 1:1 kinetic titration model with drift. Residuals (difference between data and fitted curve) are shown in the smaller top panel. (C) Percent deuteration of fragments of free and ligand-bound high affinity DMF5 variant at the 10 minute time point. Fragments including the CDR, AB, CC' and FG loops and the C and F strands are indicated. The dashed blue and red lines indicate the average deuteration of the free and bound protein, respectively.
Figure 2B:
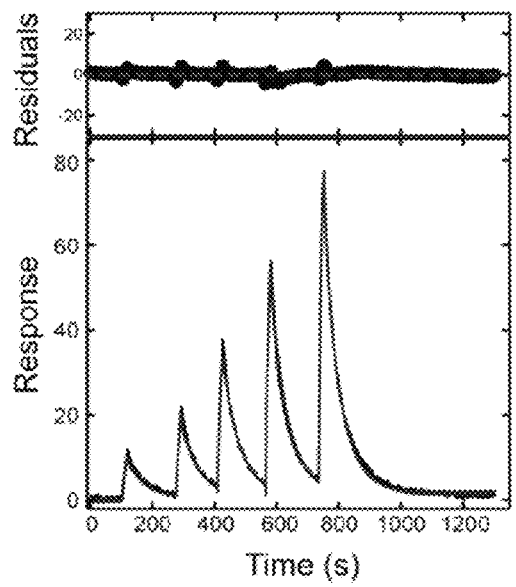

To ask if the reduction in exchange occurring upon binding was general or specific to A6, we repeated the HDX-MS experiments using the DMF5 TCR, which recognizes the MART-1$_{26-35}$ peptide presented by HLA-A2 (21). However, DMF5 binds more weakly than A6, and achieving high receptor occupancy required excess ligand concentrations that negatively impacted detection of TCR signals by MALDI mass spectrometry. We thus utilized a high affinity DMF5 variant, produced using the recently developed structure-guided TCR design algorithm ZAFFI (20). Surface plasmon resonance analysis of 10 DMF5 point mutants predicted to improve affinity identified two that when combined yielded a high-affinity DMF5 variant that included a D to Y mutation at amino acid 27 in the alpha chain (αD27Y) and a L to W mutation at amino acid 98 in the beta chain (βL95W), which bound with significantly improved affinity as compared to the wild-type (Table 1 and FIGS. 2A-B).

Figure 2C:
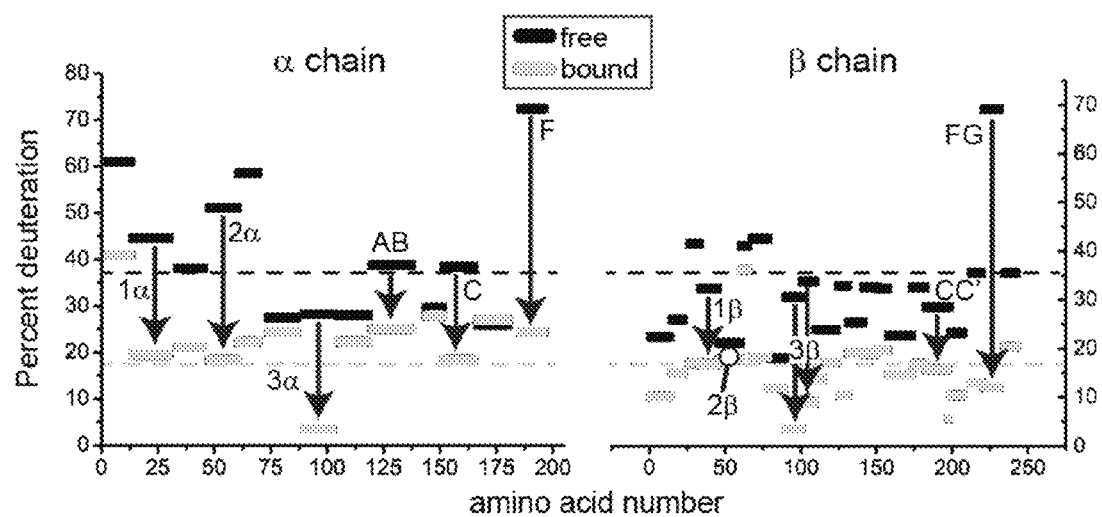

HDX-MS experiments with the high affinity DMF5 variant showed a reduction in hydrogen/deuterium exchange upon ligation that closely resembled that observed with A6 (FIG. 2C). The average deuteration of DMF5 before and after binding was 37% and 19%, respectively, with a repeat experiment yielding values of 35% and 18%. As with A6, the reduction was distributed across the TCR, and included the FG loop and the AB loop, as well as other regions implicated in TCR oligomerization or association with CD3 subunits (3).

Additional Mutations that Increase Affinity

Three additional mutations were made using the methods described above, including a D to W mutation at amino acid 27 in the alpha chain (αD27W), an A to P mutation at amino acid 55 of the alpha chain (αA55P), and a T to F mutation at amino acid 102 in the beta chain (βT102F).

The affinities of the mutants were tested and the results are shown in Table 1.

TABLE 1

| DMF5 Mutant | ELAGIGILTV/HLA-A2 | | AAGIGILTV/HLA-A2 | |
|---|---|---|---|---|
| | $K_D$ (µM) | ΔΔG, kcal/mol | $K_D$ (µM) | ΔΔG, kcal/mol |
| wild-type | 9.5 | — | 43 | — |
| αD27W | 0.68 | −1.6 | 1.1 | −2.2 |
| αD27Y | 0.46 | −1.8 | 4.5 | −1.4 |
| βL95W | 2.9 | −0.7 | 11 | −0.8 |
| αD27W/βL95W | 0.033 | −3.3 | 0.60 | −2.6 |
| αD27Y/βL95W | 0.024 | −3.5 | 1.7 | −1.9 |

Mutations at other positions were also tested, and demonstrated lower affinity; for example, αR28W had a $K_D$ of 26 µM; βF97W had a $K_D$ of 46 µM; and βT99F had an slightly improved $K_D$ of 8.9 µM.

Summary

In conclusion, the present data demonstrate that formation of a TCR-pMHC complex results in global TCR rigidification. Via entropic and packing effects, rigidification will promote associations with other neighboring proteins and strengthen the stability of existing complexes. New or strengthened assemblages could impact the density, positions, and accessibility of cytoplasmic domains and their associated kinases, as well as prime a complex to communicate a mechanical stress. Overall, these data raise the possibility that the TCR and its pMHC ligand are components of a dynamically-modulated, allosteric T cell signaling system.

REFERENCES FOR EXAMPLE 1

1. van der Merwe, P. A., and O. Dushek. 2011. Mechanisms for T cell receptor triggering. *Nat Rev Immunol* 11:47-55.
2. Deng, L., R. J. Langley, P. H. Brown, G. Xu, L. Teng, Q. Wang, M. I. Gonzales, G. G. Callender, M. I. Nishimura, S. L. Topalian, and R. A. Mariuzza. 2007. Structural basis for the recognition of mutant self by a tumor-specific, MHC class II-restricted T cell receptor. *Nat Immunol* 8:398-408.
3. Kuhns, M. S., A. T. Girvin, L. O. Klein, R. Chen, K. D. C. Jensen, E. W. Newell, J. B. Huppa, B. F. Lillemeier, M. Huse, Y.-h. Chien, K. C. Garcia, and M. M. Davis. 2010. Evidence for a functional sidedness to the $\alpha\beta$TCR. *Proceedings of the National Academy of Sciences* 107:5094-5099.
4. Beddoe, T., Z. Chen, C. S. Clements, L. K. Ely, S. R. Bushell, J. P. Vivian, L. Kjer-Nielsen, S. S. Pang, M. A. Dunstone, Y. C. Liu, W. A. Macdonald, M. A. Perugini, M. C. J. Wilce, S. R. Burrows, A. W. Purcell, T. Tiganis, S. P. Bottomley, J. McCluskey, and J. Rossjohn. 2009. Antigen Ligation Triggers a Conformational Change within the Constant Domain of the $\alpha\beta$ T Cell Receptor. *Immunity* 30:777-788.
5. Kim, S. T., K. Takeuchi, Z.-Y. J. Sun, M. Touma, C. E. Castro, A. Fahmy, M. J. Lang, G. Wagner, and E. L. Reinherz. 2009. The $\alpha\beta$ T Cell Receptor Is an Anisotropic Mechanosensor. *Journal of Biological Chemistry* 284:31028-31037.
6. Frederick, K. K., M. S. Marlow, K. G. Valentine, and A. J. Wand. 2007. Conformational entropy in molecular recognition by proteins. *Nature* 448:325-329.
7. Tobi, D., and I. Bahar. 2005. Structural changes involved in protein binding correlate with intrinsic motions of proteins in the unbound state. *Proceedings of the National Academy of Sciences* 102:18908-18913.
8. Zhang, J., M. J. Chalmers, K. R. Stayrook, L. L. Burris, Y. Wang, S. A. Busby, B. D. Pascal, R. D. Garcia-Ordonez, J. B. Bruning, M. A. Istrate, D. J. Kojetin, J. A. Dodge, T. P. Burris, and P. R. Griffin. 2011. DNA binding alters coactivator interaction surfaces of the intact VDR-RXR complex. *Nat Struct Mol Biol* 18:556-563.
9. Popovych, N., S. Sun, R. H. Ebright, and C. G. Kalodimos. 2006. Dynamically driven protein allostery. *Nat Struct Mol Biol* 13:831-838.
10. Tzeng, S.-R., and C. G. Kalodimos. 2009. Dynamic activation of an allosteric regulatory protein. *Nature* 462:368-372.
11. Smock, R. G., and L. M. Gierasch. 2009. Sending Signals Dynamically. *Science* 324:198-203.
12. Davis-Harrison, R. L., K. M. Armstrong, and B. M. Baker. 2005. Two Different T Cell Receptors use Different Thermodynamic Strategies to Recognize the Same Peptide/MHC Ligand. *Journal of Molecular Biology* 346:533-550.
13. Boulter, J. M., M. Glick, P. T. Todorov, E. Baston, M. Sami, P. Rizkallah, and B. K. Jakobsen. 2003. Stable, soluble T-cell receptor molecules for crystallization and therapeutics. *Protein Eng.* 16:707-711.
14. Ding, Y. H., B. M. Baker, D. N. Garboczi, W. E. Biddison, and D. C. Wiley. 1999. Four A6-TCR/peptide/HLA-A2 structures that generate very different T cell signals are nearly identical. *Immunity* 11:45-56.
15. Englander, S. W., T. R. Sosnick, J. J. Englander, and L. Mayne. 1996. Mechanisms and uses of hydrogen exchange. *Current Opinion in Structural Biology* 6:18-23.
16. Shilov, I. V., S. L. Seymour, A. A. Patel, A. Loboda, W. H. Tang, S. P. Keating, C. L. Hunter, L. M. Nuwaysir, and D. A. Schaeffer. 2007. The Paragon Algorithm, a Next Generation Search Engine That Uses Sequence Temperature Values and Feature Probabilities to Identify Peptides from Tandem Mass Spectra. *Molecular & Cellular Proteomics* 6:1638-1655.
17. Balgley, B. M., T. Laudeman, L. Yang, T. Song, and C. S. Lee. 2007. Comparative Evaluation of Tandem MS Search Algorithms Using a Target-Decoy Search Strategy. *Molecular & Cellular Proteomics* 6:1599-1608.
18. Eyal, E., L.-W. Yang, and I. Bahar. 2006. Anisotropic network model: systematic evaluation and a new web interface. *Bioinformatics* 22:2619-2627.
19. Scott, D. R., 0. Y. Borbulevych, K. H. Piepenbrink, S. A. Corcelli, and B. M. Baker. 2011. Disparate Degrees of Hypervariable Loop Flexibility Control T-Cell Receptor Cross-Reactivity, Specificity, and Binding Mechanism. *Journal of Molecular Biology* 414:385-400.
20. Haidar, J. N., B. Pierce, Y. Yu, W. Tong, M. Li, and Z. Weng. 2009. Structure-based design of a T-cell receptor leads to nearly 100-fold improvement in binding affinity for pepMHC. *Proteins: Structure, Function, and Bioinformatics* 74:948-960.
21. Borbulevych, O. Y., S. M. Santhanagopolan, M. Hossain, and B. M. Baker. 2011. TCRs Used in Cancer Gene Therapy Cross-React with MART-1/Melan-A Tumor Antigens via Distinct Mechanisms. *J Immunol* 187:2453-2463.
22. Kortemme, T., and D. Baker. 2002. A simple physical model for binding energy hot spots in protein-protein complexes. *Proc Natl Acad Sci USA* 99:14116-14121.
23. Varani, L., A. J. Bankovich, C. W. Liu, L. A. Colf, L. L. Jones, D. M. Kranz, J. D. Puglisi, and K. C. Garcia. 2007. Solution mapping of T cell receptor docking footprints on peptide-MHC. *Proceedings of the National Academy of Sciences* 104:13080-13085.
24. Marcsisin, S. R., and J. R. Engen. 2010. Hydrogen exchange mass spectrometry: what is it and what can it tell us? *Analytical and bioanalytical chemistry* 397:967-972.
25. Laine, O., E. D. Streaker, M. Nabavi, C. C. Fenselau, and D. Beckett. 2008. Allosteric Signaling in the Biotin Repressor Occurs via Local Folding Coupled to Global Dampening of Protein Dynamics. *Journal of Molecular Biology* 381:89-101.
26. Kim, S. T., M. Touma, K. Takeuchi, Z.-Y. J. Sun, V. P. Dave, D. J. Kappes, G. Wagner, and E. L. Reinherz. 2010. Distinctive CD3 Heterodimeric Ectodomain Topologies Maximize Antigen-Triggered Activation of $\alpha\beta$ T Cell Receptors. *The Journal of Immunology* 185:2951-2959.
27. Martinez-Martin, N., R. M. Risueno, A. Morreale, I. Zaldivar, E. Fernandez-Arenas, F. Herranz, A. R. Ortiz, and B. Alarcon. 2009. Cooperativity Between T Cell Receptor Complexes Revealed by Conformational Mutants of CD3 {varepsilon}. *Sci. Signal.* 2:ra43-.
28. Bahar, I., T. R. Lezon, L.-W. Yang, and E. Eyal. 2010. Global Dynamics of Proteins: Bridging Between Structure and Function. *Annual Review of Biophysics* 39:23-42.
29. Ma, B., C.-J. Tsai, T. Haliloğlu, and R. Nussinov. 2011. Dynamic Allostery: Linkers Are Not Merely Flexible. *Structure* 19:907-917.
30. Gagnon, S. J., 0. Y. Borbulevych, R. L. Davis-Harrison, R. V. Turner, M. Damirjian, A. Wojnarowicz, W. E. Biddison, and B. M. Baker. 2006. T Cell Receptor Recognition via Cooperative Conformational Plasticity. *Journal of Molecular Biology* 363:228-243.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A high-affinity DMF5 T cell receptor variant α chain, wherein the aspartic amino acid at position 27 or 49 is a Y (αD27Y or αD49Y) or W (αD27W or αD49W).

2. A high-affinity DMF5 T cell receptor variant β chain, wherein the leucine amino acid at position 95, 96 or 114 is a W (βL95W, βL96W βL114W).

3. A high-affinity DMF5 T cell receptor variant comprising:
   a high-affinity DMF5 T cell receptor variant α chain, wherein the aspartic amino acid at
   position 27 or 49 is a Y (αD27Y or αD49Y) or W (αD27W or αD49W), and
   a high-affinity DMF5 T cell receptor variant β chain, wherein the leucine amino acid at position 95, 96 or 114 is a W (βL95W, βL96W βL114W).

4. A fusion protein comprising the high-affinity DMF5 T cell receptor variant of claim 3 linked to a non-TCR sequence.

5. A therapeutic composition comprising:
   a therapeutic agent linked to
   the high-affinity DMF5 T cell receptor variant of claim 3, optionally linked to a non-TCR sequence.

6. The therapeutic composition of claim 5, wherein the therapeutic agent is a radioisotope; an anticancer drug; or a cytotoxic moiety.

7. A composition comprising:
   a detectable moiety linked to
   the high-affinity DMF5 T cell receptor variant of claim 3, optionally linked to a non-TCR sequence.

8. The composition of claim 7, wherein the detectable moiety is a contrast agent.

9. The composition of claim 8, wherein the contrast agent is selected from the group consisting of gold, gadolinium, iron oxides, manganese chelates, barium sulfate, iodinated contrast media, microbubbles, and perfluorocarbons.

10. A nucleic acid encoding:
    the high-affinity DMF5 T cell receptor variant of claim 3, optionally linked to a non-TCR sequence.

11. A vector comprising the nucleic acid of claim 10.

12. The vector of claim 11, which is a retroviral vector.

13. A host cell expressing:
    the high-affinity DMF5 T cell receptor variant of claim 3, optionally linked to a non-TCR sequence.

14. A host cell comprising the nucleic acid of claim 10.

15. The host cell of claim 14, wherein the cell is a peripheral blood lymphocyte (PBL).

16. A method of treating a subject who has melanoma, the method comprising administering to the subject a therapeutically effective amount of the therapeutic composition of claim 5.

17. A method of treating a subject who has melanoma, the method comprising administering to the subject a therapeutically effective amount of the host cells of claim 14.

18. The method of claim 17, wherein the host cells are autologous to the subject.

19. A method of treating a subject who has melanoma, the method comprising:
    obtaining cells from the subject;
    transducing the cells with a vector expressing:
    the high-affinity DMF5 T cell receptor variant of claim 3, optionally linked to a non-TCR sequence;
    optionally maintaining the cells in culture for a time sufficient for the cells to express the variant or fusion protein and/or to proliferate; and
    administering a therapeutically effective amount of the cells to the subject thereafter.

20. The method of claim 19, wherein the cells are PBLs.

* * * * *

UNITED STATES PATENT AND TRADEMARK OFFICE
CERTIFICATE OF CORRECTION

PATENT NO. : 9,717,758 B2
APPLICATION NO. : 14/280308
DATED : August 1, 2017
INVENTOR(S) : Brian G. Pierce, Zhiping Weng and Brian M. Baker It is certified that error appears in the above-identified patent and that said Letters Patent is hereby corrected as shown below:

Column 41, Line 16, in Claim 1, after "βL96W" insert --or--.

Column 41, Line 25, in Claim 3, after "βL96W" insert --or--.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*

```
                         SEQUENCE LISTING

<160> NUMBER OF SEQ ID NOS: 8

<210> SEQ ID NO 1
<211> LENGTH: 253
<212> TYPE: PRT
<213> ORGANISM: homo sapiens
<220> FEATURE:
<223> OTHER INFORMATION: DMF5 TCR alpha chain

<400> SEQUENCE: 1

Gln Lys Glu Val Glu Gln Asn Ser Gly Pro Leu Ser Val Pro Glu Gly
 1               5                  10                  15

Ala Ile Ala Ser Leu Asn Cys Thr Tyr Ser Ala Ser Pro Arg Gly Ser
                20                  25                  30

Gln Ser Phe Phe Trp Tyr Arg Gln Tyr Ser Gly Lys Ser Pro Glu Leu
            35                  40                  45

Ile Met Phe Ile Tyr Ser Asn Gly Asp Lys Glu Asp Gly Arg Phe Thr
        50                  55                  60

Ala Gln Leu Asn Lys Ala Ser Gln Tyr Val Ser Leu Leu Ile Arg Asp
65                  70                  75                  80

Ser Gln Pro Ser Asp Ser Ala Thr Tyr Leu Cys Ala Val Asn Phe Gly
                85                  90                  95

Gly Gly Lys Leu Ile Phe Gly Gln Gly Thr Glu Leu Ser Val Lys Pro
            100                 105                 110

Asn Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
    130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser Cys Asp
        195                 200                 205

Val Lys Leu Val Glu Lys Ser Phe Glu Thr Asp Thr Asn Leu Asn Phe
    210                 215                 220

Gln Asn Leu Ser Val Ile Gly Phe Arg Ile Leu Leu Leu Lys Val Ala
225                 230                 235                 240

Gly Phe Asn Leu Leu Met Thr Leu Arg Leu Trp Ser Ser
                245                 250

<210> SEQ ID NO 2
<211> LENGTH: 288
<212> TYPE: PRT
<213> ORGANISM: homo sapiens
<220> FEATURE:
<223> OTHER INFORMATION: DMF5 TCR beta chain

<400> SEQUENCE: 2

Ile Ala Gly Ile Thr Gln Ala Pro Thr Ser Gln Ile Leu Ala Ala Gly
 1               5                  10                  15
```

```
Arg Arg Met Thr Leu Arg Cys Thr Gln Asp Met Arg His Asn Ala Met
             20                  25                  30

Tyr Trp Tyr Arg Gln Asp Leu Gly Leu Gly Leu Arg Leu Ile His Tyr
         35                  40                  45

Ser Asn Thr Ala Gly Thr Thr Gly Lys Gly Glu Val Pro Asp Gly Tyr
 50                  55                  60

Ser Val Ser Arg Ala Asn Thr Asp Asp Phe Pro Leu Thr Leu Ala Ser
 65                  70                  75                  80

Ala Val Pro Ser Gln Thr Ser Val Tyr Phe Cys Ala Ser Ser Leu Glu
                 85                  90                  95

Ser Phe Gly Thr Glu Ala Phe Phe Gly Gln Gly Thr Arg Leu Thr Val
             100                 105                 110

Val Glu Asp Leu Asn Lys Val Phe Pro Pro Glu Val Ala Val Phe Glu
         115                 120                 125

Pro Ser Glu Ala Glu Ile Ser His Thr Gln Lys Ala Thr Leu Val Cys
130                 135                 140

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                 165                 170                 175

Lys Glu Gln Pro Ala Leu Asn Asp Ser Arg Tyr Cys Leu Ser Ser Arg
             180                 185                 190

Leu Arg Val Ser Ala Thr Phe Trp Gln Asn Pro Arg Asn His Phe Arg
         195                 200                 205

Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Cys Gly Phe Thr Ser Ser Tyr Gln Gln Gly Val Leu Ser Ala
                 245                 250                 255

Thr Ile Leu Tyr Glu Ile Leu Leu Gly Lys Ala Thr Leu Tyr Ala Val
             260                 265                 270

Leu Val Ser Ala Leu Val Leu Met Ala Met Val Lys Arg Lys Asp Phe
         275                 280                 285

<210> SEQ ID NO 3
<211> LENGTH: 133
<212> TYPE: PRT
<213> ORGANISM: homo sapiens
<220> FEATURE:
<223> OTHER INFORMATION: DMF5 TCR alpha chain variant

<400> SEQUENCE: 3

Met Met Lys Ser Leu Arg Val Leu Leu Val Ile Leu Trp Leu Gln Leu
 1               5                  10                  15

Ser Trp Val Trp Ser Gln Gln Lys Glu Val Glu Gln Asn Ser Gly Pro
             20                  25                  30

Leu Ser Val Pro Glu Gly Ala Ile Ala Ser Leu Asn Cys Thr Tyr Ser
         35                  40                  45

Asp Arg Gly Ser Gln Ser Phe Phe Trp Tyr Arg Gln Tyr Ser Gly Lys
 50                  55                  60

Ser Pro Glu Leu Ile Met Phe Ile Tyr Ser Asn Gly Asp Lys Glu Asp
 65                  70                  75                  80

Gly Arg Phe Thr Ala Gln Leu Asn Lys Ala Ser Gln Tyr Val Ser Leu
                 85                  90                  95
```

```
Leu Ile Arg Asp Ser Gln Pro Ser Asp Ser Ala Thr Tyr Leu Cys Ala
            100                 105                 110

Val Asn Phe Gly Gly Gly Lys Leu Ile Phe Gly Gln Gly Thr Glu Leu
            115                 120                 125

Ser Val Lys Pro Asn
    130

<210> SEQ ID NO 4
<211> LENGTH: 131
<212> TYPE: PRT
<213> ORGANISM: homo sapiens
<220> FEATURE:
<223> OTHER INFORMATION: DMF5 TCR beta chain variant

<400> SEQUENCE: 4

Met Arg Ile Arg Leu Leu Cys Cys Val Ala Phe Ser Leu Leu Trp Ala
1               5                   10                  15

Gly Pro Val Ile Ala Gly Ile Thr Gln Ala Pro Thr Ser Gln Ile Leu
            20                  25                  30

Ala Ala Gly Arg Arg Met Thr Leu Arg Cys Thr Gln Asp Met Arg His
            35                  40                  45

Asn Ala Met Tyr Trp Tyr Arg Gln Asp Leu Gly Leu Gly Leu Arg Leu
    50                  55                  60

Ile His Tyr Ser Asn Thr Ala Gly Thr Thr Gly Lys Gly Glu Val Pro
65                  70                  75                  80

Asp Gly Tyr Ser Val Ser Arg Ala Asn Thr Asp Asp Phe Pro Leu Thr
                85                  90                  95

Leu Ala Ser Ala Val Pro Ser Gln Thr Ser Val Tyr Phe Cys Ala Ser
            100                 105                 110

Ser Leu Ser Phe Gly Thr Glu Ala Phe Phe Gly Gln Gly Thr Arg Leu
            115                 120                 125

Thr Val Val
    130

<210> SEQ ID NO 5
<211> LENGTH: 202
<212> TYPE: PRT
<213> ORGANISM: homo sapiens
<220> FEATURE:
<223> OTHER INFORMATION: DMF5 TCR alpha chain variant

<400> SEQUENCE: 5

Ala Lys Glu Val Glu Gln Asn Ser Gly Pro Leu Ser Val Pro Glu Gly
1               5                   10                  15

Ala Ile Ala Ser Leu Asn Cys Thr Tyr Ser Asp Arg Gly Ser Gln Ser
            20                  25                  30

Phe Phe Trp Tyr Arg Gln Tyr Ser Gly Lys Ser Pro Glu Leu Ile Met
            35                  40                  45

Phe Ile Tyr Ser Asn Gly Asp Lys Glu Asp Gly Arg Phe Thr Ala Gln
    50                  55                  60

Leu Asn Lys Ala Ser Gln Tyr Val Ser Leu Leu Ile Arg Asp Ser Gln
65                  70                  75                  80

Pro Ser Asp Ser Ala Thr Tyr Leu Cys Ala Val Asn Phe Gly Gly Gly
                85                  90                  95

Lys Leu Ile Phe Gly Gln Gly Thr Glu Leu Ser Val Lys Pro Asn Ile
            100                 105                 110

Gln Asn Pro Asp Pro Ala Val Tyr Gln Leu Arg Asp Ser Lys Ser Ser
            115                 120                 125
```

Asp Lys Ser Val Cys Leu Phe Thr Asp Phe Asp Ser Gln Thr Asn Val
            130                 135                 140

Ser Gln Ser Lys Asp Ser Asp Val Tyr Ile Thr Asp Lys Cys Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
                180                 185                 190

Pro Glu Asp Thr Phe Phe Pro Ser Pro Glu
                195                 200

<210> SEQ ID NO 6
<211> LENGTH: 243
<212> TYPE: PRT
<213> ORGANISM: homo sapiens
<220> FEATURE:
<223> OTHER INFORMATION: DMF5 TCR beta chain variant

<400> SEQUENCE: 6

Met Ile Ala Gly Ile Thr Gln Ala Pro Thr Ser Gln Ile Leu Ala Ala
1               5                   10                  15

Gly Arg Arg Met Thr Leu Arg Cys Thr Gln Asp Met Arg His Asn Ala
                20                  25                  30

Met Tyr Trp Tyr Arg Gln Asp Leu Gly Leu Gly Leu Arg Leu Ile His
            35                  40                  45

Tyr Ser Asn Thr Ala Gly Thr Thr Gly Lys Gly Glu Val Pro Asp Gly
50                  55                  60

Tyr Ser Val Ser Arg Ala Asn Thr Asp Asp Phe Pro Leu Thr Leu Ala
65                  70                  75                  80

Ser Ala Val Pro Ser Gln Thr Ser Val Tyr Phe Cys Ala Ser Ser Leu
                85                  90                  95

Ser Phe Gly Thr Glu Ala Phe Phe Gly Gln Gly Thr Arg Leu Thr Val
                100                 105                 110

Val Glu Asp Leu Asn Lys Val Phe Pro Pro Glu Val Ala Val Phe Glu
                115                 120                 125

Pro Ser Glu Ala Glu Ile Ser His Thr Gln Lys Ala Thr Leu Val Cys
130                 135                 140

Leu Ala Thr Gly Phe Tyr Pro Asp His Val Glu Leu Ser Trp Trp Val
145                 150                 155                 160

Asn Gly Lys Glu Val His Ser Gly Val Cys Thr Asp Pro Gln Pro Leu
                165                 170                 175

Lys Glu Gln Pro Ala Leu Asn Asp Ser Arg Tyr Ala Leu Ser Ser Arg
                180                 185                 190

Leu Arg Val Ser Ala Thr Phe Trp Gln Asp Pro Arg Asn His Phe Arg
                195                 200                 205

Cys Gln Val Gln Phe Tyr Gly Leu Ser Glu Asn Asp Glu Trp Thr Gln
            210                 215                 220

Asp Arg Ala Lys Pro Val Thr Gln Ile Val Ser Ala Glu Ala Trp Gly
225                 230                 235                 240

Arg Ala Asp

<210> SEQ ID NO 7
<211> LENGTH: 399
<212> TYPE: PRT
<213> ORGANISM: homo sapiens
<220> FEATURE:

<223> OTHER INFORMATION: wild type DMF5 Valpha

<400> SEQUENCE: 7

```
Ala Thr Gly Ala Thr Gly Ala Ala Thr Cys Cys Thr Thr Gly Ala
 1               5                  10                  15
Gly Ala Gly Thr Thr Thr Thr Ala Cys Thr Ala Gly Thr Gly Ala Thr
             20                  25                  30
Cys Cys Thr Gly Thr Gly Gly Cys Thr Cys Ala Gly Thr Thr Gly
         35                  40                  45
Ala Gly Cys Thr Gly Gly Gly Thr Thr Gly Gly Ala Gly Cys Cys
     50                  55                  60
Ala Ala Cys Ala Gly Ala Ala Gly Gly Ala Gly Thr Gly Gly Ala
65                  70                  75                  80
Gly Cys Ala Gly Ala Ala Thr Thr Cys Thr Gly Gly Ala Cys Cys
         85                  90                  95
Cys Thr Cys Ala Gly Thr Gly Thr Thr Cys Cys Ala Gly Ala Gly Gly
         100                 105                 110
Gly Ala Gly Cys Cys Ala Thr Thr Gly Cys Cys Thr Cys Thr Cys Thr
         115                 120                 125
Cys Ala Ala Cys Thr Gly Cys Ala Cys Thr Thr Ala Cys Ala Gly Thr
         130                 135                 140
Gly Ala Cys Cys Gly Ala Gly Gly Thr Thr Cys Cys Cys Ala Gly Thr
145                 150                 155                 160
Cys Cys Thr Thr Cys Thr Thr Cys Thr Gly Gly Thr Ala Cys Ala Gly
                 165                 170                 175
Ala Cys Ala Ala Thr Ala Thr Thr Cys Thr Gly Gly Ala Ala Ala
             180                 185                 190
Ala Gly Cys Cys Cys Thr Gly Ala Gly Thr Thr Gly Ala Thr Ala Ala
             195                 200                 205
Thr Gly Thr Thr Cys Ala Thr Ala Thr Cys Thr Cys Cys Ala Ala
         210                 215                 220
Thr Gly Gly Thr Gly Ala Cys Ala Ala Ala Gly Ala Ala Gly Ala Thr
225                 230                 235                 240
Gly Gly Ala Ala Gly Gly Thr Thr Thr Ala Cys Ala Gly Cys Ala Cys
                 245                 250                 255
Ala Gly Cys Thr Cys Ala Ala Thr Ala Ala Gly Cys Cys Ala Gly
             260                 265                 270
Cys Cys Ala Gly Thr Ala Thr Gly Thr Thr Thr Cys Thr Cys Thr Gly
             275                 280                 285
Cys Thr Cys Ala Thr Cys Ala Gly Ala Gly Ala Cys Thr Cys Cys Cys
         290                 295                 300
Ala Gly Cys Cys Cys Ala Gly Thr Gly Ala Thr Thr Cys Ala Gly Cys
305                 310                 315                 320
Cys Ala Cys Cys Thr Ala Cys Cys Thr Cys Thr Gly Thr Gly Cys Cys
                 325                 330                 335
Gly Thr Gly Ala Ala Cys Thr Thr Cys Gly Gly Ala Gly Gly Ala Gly
             340                 345                 350
Gly Ala Ala Ala Gly Cys Thr Thr Ala Thr Cys Thr Thr Cys Gly Gly
             355                 360                 365
Ala Cys Ala Gly Gly Gly Ala Ala Cys Gly Gly Ala Gly Thr Thr Ala
         370                 375                 380
Thr Cys Thr Gly Thr Gly Ala Ala Cys Cys Cys Ala Ala Thr
385                 390                 395
```

<210> SEQ ID NO 8
<211> LENGTH: 393
<212> TYPE: PRT
<213> ORGANISM: homo sapiens
<220> FEATURE:
<223> OTHER INFORMATION: wild type DMF5 V beta

<400> SEQUENCE: 8

```
Ala Thr Gly Ala Gly Ala Ala Thr Cys Ala Gly Gly Cys Thr Cys Cys
 1               5                  10                  15

Thr Gly Thr Gly Cys Thr Gly Thr Gly Thr Gly Gly Cys Cys Thr Thr
            20                  25                  30

Thr Thr Cys Thr Cys Thr Cys Cys Thr Gly Thr Gly Gly Gly Cys Ala
        35                  40                  45

Gly Gly Thr Cys Cys Ala Gly Thr Gly Ala Thr Thr Gly Cys Thr Gly
    50                  55                  60

Gly Gly Ala Thr Cys Ala Cys Cys Cys Ala Gly Gly Cys Ala Cys Cys
65                  70                  75                  80

Ala Ala Cys Ala Thr Cys Thr Cys Ala Gly Ala Thr Cys Cys Thr Gly
                85                  90                  95

Gly Cys Ala Gly Cys Ala Gly Gly Ala Cys Gly Gly Cys Gly Cys Ala
            100                 105                 110

Thr Gly Ala Cys Ala Cys Thr Gly Ala Gly Ala Thr Gly Thr Ala Cys
        115                 120                 125

Cys Cys Ala Gly Gly Ala Thr Ala Thr Gly Ala Gly Ala Cys Ala Thr
    130                 135                 140

Ala Ala Thr Gly Cys Cys Ala Thr Gly Thr Ala Cys Thr Gly Gly Thr
145                 150                 155                 160

Ala Thr Ala Gly Ala Cys Ala Ala Gly Ala Thr Cys Thr Ala Gly Gly
                165                 170                 175

Ala Cys Thr Gly Gly Gly Gly Cys Thr Ala Ala Gly Gly Cys Thr Cys
            180                 185                 190

Ala Thr Cys Cys Ala Thr Thr Ala Thr Thr Cys Ala Ala Ala Thr Ala
        195                 200                 205

Cys Thr Gly Cys Ala Gly Gly Thr Ala Cys Cys Ala Cys Thr Gly Gly
    210                 215                 220

Cys Ala Ala Ala Gly Gly Ala Gly Ala Ala Gly Thr Cys Cys Cys Thr
225                 230                 235                 240

Gly Ala Thr Gly Gly Thr Thr Ala Thr Ala Gly Thr Gly Thr Cys Thr
                245                 250                 255

Cys Cys Ala Gly Ala Gly Cys Ala Ala Ala Cys Ala Cys Ala Gly Ala
            260                 265                 270

Thr Gly Ala Thr Thr Thr Cys Cys Cys Cys Cys Thr Cys Ala Cys Gly
        275                 280                 285

Thr Thr Gly Gly Cys Gly Thr Cys Thr Gly Cys Thr Gly Thr Ala Cys
    290                 295                 300

Cys Cys Thr Cys Thr Cys Ala Gly Ala Cys Ala Thr Cys Thr Gly Thr
305                 310                 315                 320

Gly Thr Ala Cys Thr Thr Cys Thr Gly Thr Gly Cys Cys Ala Gly Cys
                325                 330                 335

Ala Gly Cys Cys Thr Ala Ala Gly Thr Thr Thr Cys Gly Gly Cys Ala
            340                 345                 350

Cys Thr Gly Ala Ala Gly Cys Thr Thr Thr Cys Thr Thr Thr Gly Gly
        355                 360                 365
```

```
Ala Cys Ala Ala Gly Gly Cys Ala Cys Cys Ala Gly Ala Cys Thr Cys
    370                 375                 380
Ala Cys Ala Gly Thr Thr Gly Thr Ala
385                 390
```